(12) United States Patent
Hasserodt et al.

(10) Patent No.: US 11,078,226 B2
(45) Date of Patent: Aug. 3, 2021

(54) FLUOROGENIC GLYCOSIDASE SUBSTRATE AND ASSOCIATED DETECTION METHOD

(71) Applicants: ECOLE NORMALE SUPERIEURE DE LYON, Lyons (FR); UNIVERSITE CLAUDE BERNARD LYON, Villeurbanne (FR); CENTRE NATIONAL DE LA RECHERCHE SCIENTIFIQUE, Paris (FR)

(72) Inventors: Jens Hasserodt, Sainte-Foy-les-Lyon (FR); Corentin Gondrand, Heidelberg (DE); Maxime Prost, Lyons (FR); Gaël Yvert, Saint-Genis-Laval (FR); Gérard Triqueneaux, Lyons (FR)

(73) Assignees: ECOLE NORMALE SUPERIEURE DE LYON, Lyons (FR); UNIVERSITE CLAUDE BERNARD LYON 1, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/471,153

(22) PCT Filed: Dec. 19, 2017

(86) PCT No.: PCT/EP2017/083518
§ 371 (c)(1),
(2) Date: Jun. 19, 2019

(87) PCT Pub. No.: WO2018/114933
PCT Pub. Date: Jun. 28, 2018

(65) Prior Publication Data
US 2020/0002367 A1 Jan. 2, 2020

(30) Foreign Application Priority Data

Dec. 19, 2016 (FR) ...................................... 1662787

(51) Int. Cl.
*C07H 15/203* (2006.01)
*C07H 17/02* (2006.01)
*C12Q 1/34* (2006.01)
*G01N 33/574* (2006.01)
*G01N 33/68* (2006.01)

(52) U.S. Cl.
CPC .......... *C07H 15/203* (2013.01); *C07H 17/02* (2013.01); *C12Q 1/34* (2013.01); *G01N 33/574* (2013.01); *G01N 33/6893* (2013.01); *G01N 2333/924* (2013.01)

(58) Field of Classification Search
CPC ...... C07H 15/20; C07H 15/203; C07H 17/02; A61K 43/00; G01H 33/574; G01H 2333/924; G01H 33/6893; G01N 33/574; G01N 2333/924; G01N 33/6893

USPC .......................................................... 536/4.1
See application file for complete search history.

(56) References Cited

U.S. PATENT DOCUMENTS

| 2009/0081634 A1 | 3/2009 | Durrat et al. |
| 2014/0234887 A1 | 8/2014 | Hasserodt et al. |
| 2015/0299762 A1 | 10/2015 | Hasserodt |
| 2017/0159100 A1 | 6/2017 | Hasserodt et al. |

FOREIGN PATENT DOCUMENTS

| EP | 2 033 633 A2 | 3/2009 | |
| WO | 2004/058787 A2 | 7/2004 | |
| WO | WO 2008/153394 A2 * | 12/2008 | ............. C07H 15/18 |
| WO | 2013/045854 A1 | 4/2013 | |
| WO | 2014/020285 A1 | 2/2014 | |
| WO | 2015/197981 A1 | 12/2015 | |

OTHER PUBLICATIONS

Schuster et al, Org. Biomol. Chem. 2010, 8, 1833-1842.*
Schuster et al, Organic & Biomolecular Chemistry 2010, 8, 1833-1842; published on the web on Feb. 17, 2010.*
Xue et al.; "Kinetic delay of cyclization/elimination-coupled enzyme assays: Analysis and solution;" Bioorganic & Medicinal Chemistry Letters; 2011; pp. 1069-1071; vol. 21, No. 3.
De Groot et al.; "Elongated Multiple Electronic Cascade and Cyclization Spacer Systems in Activatible Anticancer Prodrugs for Enhanced Drug Release;" J. Org. Chem.; 2001; pp. 8815-8830; vol. 66.
Jan. 31, 2018 Search Report issued in International Patent Application No. PCT/EP2017/083518.
Jan. 31, 2018 Written Opinion of the International Searching Authority issued in International Patent Application No. PCT/EP2017/083518.

* cited by examiner

*Primary Examiner* — Ganapathy Krishnan
(74) *Attorney, Agent, or Firm* — Oliff PLC

(57) ABSTRACT

The invention relates to novel glycosidase substrates of formula (I), wherein R1, R2, R3, R4, R5, R6, R7, R8, R9, R'9, V, X, Y and Z are as defined in claim 1, and a method for detecting the presence of a catalytically active glycosidase by means of one of said substrates.

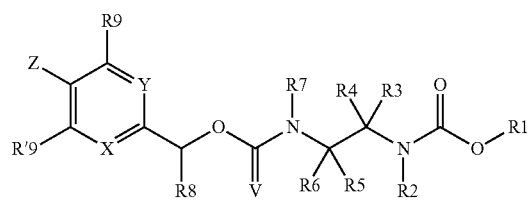

21 Claims, 3 Drawing Sheets

FLUOROGENIC GLYCOSIDASE SUBSTRATE AND ASSOCIATED DETECTION METHOD

This invention relates to probes for the detection of glycosidase-type enzymatic activity. In particular, the invention relates to novel fluorogenic substrates for detecting the presence of a catalytically active glycosidase and a detection method using such substrates.

In the analysis of a biological or chemical sample, the detection of a glycosidase activity can be very useful (Boonacker E. and Van Noorden C. J. F. (2001). Enzyme cytochemical techniques for metabolic mapping in living cells, with special reference to proteolysis. J. Histochem. Cytochem. 49, 1473-1486; Perry, 1. D., James, A. L., Ptorris, K. A., Oliver, M., Chilvers, K. F., Reed, R. H., & Gould, F. K. (2006). Evaluation of novel fluorogenic substrates for the detection of glycosidases in *Escherichia coli* and enterococci. Journal of Applied Microbiology, 101(5), 977-985; Orenga, S., James, A. L., Manafi, M., Perry, 1. D., & Pincus, D. H. (2009). Enzymatic substrates in microbiology. Journal of Microbiological Methods, 79(2), 139-155). Whole organisms, cells or cellular extracts, biological fluids or chemical mixtures are examples of biological or chemical samples in with glycosidase activity can be detected. Glycosidases are a vast family of enzymes which includes numerous biomarkers for diverse pathologies. They are also involved in numerous benign cellular processes and are, therefore the subject of innumerable studies by cellular biologists. Thus, their detection can give information regarding a specific metabolic state or morbid condition, for example. Effective detection also makes it possible to implement high-throughput screens, making it possible to detect novel, natural glycosidases, or to develop novel glycosidases by directed evolution of known enzymes, or to improve the glycolytic yield of certain micro-organisms through mutagenesis or experimental evolution of their genome.

For this reason, a probe capable of detecting glycosidase activity is very useful.

The detection of this activity by the capture of fluorescent light issued by a probe is a much more sensitive method than the collection of white light remnants during a simple absorption by the probe, that is, the detection threshold is much lower. Detection of a fluorescence emission is very easy to implement, so that fluorescent probes are very attractive tools for the life sciences. For example, the class of fluorophores leading to an intramolecular proton transfer in an excited state, called ESIPT (ESIPT, from English, "Excited State Intramolecular Proton Transfer"), is described, specifically, in a) Ormson, S. M., et al. Progress in Reaction Kinetics (1994) 19, 45-91; b) Legourrierec, D., et al. Progress in Reaction Kinetics (1994), 19, 211-275; and c) Zhao, 1., Ji, S., Chen, Y., Guo, H., & Yang, P. (2012). Excited state intramolecular proton transfer (ESIPT): from principal photo physics to the development of new chromophores and applications in fluorescent molecular probes and luminescent materials. Physical Chemistry Chemical Physics, 14 (25), 8803. The first interpretation of the elevated fluorescence found in certain phenolic compounds as being an ESIPT phenomenon can be attributed to Weller (for methyl salicylate: Weller, A. (1961). Fast Reactions of Excited Molecules. Progress in Reaction Kinetics and Mechanism 1, 187), and to Heller and Williams (for hydroxyphenyl benzoxazoles: Heller A., et Williams, D. L., 1. Phys. Chem. (1970) 74, 4473-4480). The class of ESIPT fluorophores is especially attractive to the researcher in the life sciences, due to its exceptional properties in comparison with the conventional fluorophores. The exceptional properties of the ESIPT fluorophores are:

(a) a large Stokes shift often exceeding 130 nm and capable of reaching values of 250 nm which makes instrumental choices possible that maximize the sensitivity of detection; an excellent resistance to photo bleaching with rates that may be several orders of magnitude greater than those of model fluorophores such as fluorescein;

(c) the ability to design fluorophores that emit a brilliant fluorescence in the solid state, a property that is rare among all known fluorophores. This last characteristic makes it possible to produce a high-intensity signal at the activation site, with minimum dilution caused by diffusion;

(d) the ability to design ESIPT fluorophores which issue in the red, or nearly infrared (600 to 850 nm) where tissue transparency is the greatest; a probe using such fluorophores would also be especially suited for imaging in a living animal; and finally, (e) the ability to design a substrate not issuing fluorescence by replacing the hydrogen atom borne by the hydroxyl of an ESIPT fluorophore with a substitute which has a specific reactivity in relation to a chemical or biochemical analyte, the cleavage of this substitute driving the appearance of the fluorescence.

The sensitivity level of a detection method for enzymatic activity, by use of a substrate resulting in a production of fluorescence, is closely linked (i) to the rate of photo bleaching, (ii) to the degree of accumulation of the fluorescent signal on its production site (and, therefore, to the diffusion rate from this site, and to the question of knowing if the fluorophore precipitates or not) (iii) to the actual extinguishing/lighting mode according to which the substrate functions (lack of background which would be due to a fluorescence of untransformed substrate), and (iv) to the degree of excitation spectrum and emission spectrum stacking (their separation at the baseline being the most favorable configuration; see point a) above). Point (iv) is of a very specific importance, because complete separation at the baseline provides the opportunity of a very broad choice of filters for the light source (in order to excite the fluorophore at every possible wavelength), but even more importantly, for the detector (in order to harvest photons coming from all of the wavelengths issued by the fluorophore). Point (iv) also minimizes disturbance of the detection process by tissue auto-fluorescence (characterized by a weak Stokes shift of natural fluorophores), a recurring problem encountered with established fluorophores, which themselves also have a weak Stokes shift.

Among the important class of ESIPT fluorophores, dichloro-HPQ (6-chloro-2-(5-chloro-2-hydroxyphenyl)-4 (3H)-quinazolinone; CAS number: 28683-92-3) is especially interesting, given that it is completely insoluble in aqueous/physiological media, while also being highly fluorescent in the solid state and only in the solid state. Nonetheless, it is very difficult to use dichloro-HPQ in the design of a molecular probe which provides information on the activity of a glycosidase. Furthermore, the principal activities for which an HPQ based probe has already been designed (and commercialized) are those of phosphatases, due to the impossibility of creating a stable HPQ based probe with a glycosylated phenolic hydroxyl because the resulting product is inclined to rapid spontaneous hydrolysis which, it is well understood, releases the free, insoluble dichloro-HPQ and thus produces an erroneous fluorescent signal ("bottom signal"). It should also be noted that the commercialization by Molecular Probes of such glycosylated compounds (ELF 97 glucuronidase substrate (No.

E6587) and ELF 97 chitinase substrate/N-acetyl glucosaminidase (No. E22011) was interrupted in 2008 due to the intrinsic hydrolysis instability of the phenolic glycosides, and in particular of those built using phenols low in electrons, such as dichloro-HPQ. In fact, it is known that any nitrophenol-based glycoside (which is also a phenol poor in electrons like dichloro-HPQ) will hydrolyse spontaneously at physiological pH. It is also known that this stability problem is seriously aggravated at more acid pHs (for example, a pH of 6.5), in comparison with physiological pH (pH 7.4).

In recent years, there has been a growing interest in the design of enzyme substrates with several release/spacer/fluorophore components by using self-immolative spacers as the bonding agent. We may specifically cite the work of one of the inventors of this patent application corresponding to applications WO 2013/045854, WO 2014/020285 and WO 2015/197981 which use a self-folding spacer bonding a peptidase and/or glycosidase substrate to an aryl group driving, after cleavage of the substrate, the cyclization of the spacer and the release of an ESIPT fluorophore. However, with existing technologies, the detection of glycosidases is not reliable enough (the probes are unstable and release fluorescence in the absence of the target enzyme), requires too much time (the enzymatic response is too slow) and/or is not precise enough (the released fluorophore does not precipitate at one point but diffuses throughout the medium).

In this context, the Applicants propose novel glycosidase enzyme substrates offering an especially rapid enzymatic response kinetics. The invention proposes to use a novel spacer which makes it possible to create a stable probe, adapted to the incorporation of an ESIPT fluorophore, with, thus, a minimization of background fluorescence from the unprocessed probe, and which makes possible a significant increase in sensitivity, and therefore, could lead to a reduction in the quantity to be used and could thus, specifically, make an in vivo imaging application possible, while reducing toxicity problems.

The objective of the invention is to propose novel glycosidase substrates which are stable in an aqueous medium and which remain non-fluorescent or mildly fluorescent at a wavelength that is very different from that at which the released fluorophore is itself fluorescent, but which react rapidly with glycosidases in order to produce a small fluorescent molecule corresponding to an ESIPT fluorophore. According to the invention, a glycosidase substrate that has the following properties is proposed:
- a high specificity for a particular glycosidase, as a function of the choice of the glycosyl group present on the probe;
- a lack of background fluorescence due to high stability of the probe in the absence of the target enzyme, a precipitation of the fluorophore on the enzyme site and a lack of diffusion of the fluorophore in the medium; and
- rapid processing kinetics under the action of the target glycosidase.

The glycosidase substrate according to the invention thus makes it possible to preserve the glycosidase substrates of the prior art (i.e. High specificity for a particular glycosidase and lack of background fluorescence), while having rapid processing kinetics under the action of the target glycosidase.

More specifically, the invention concerns the compounds of the formula (I):

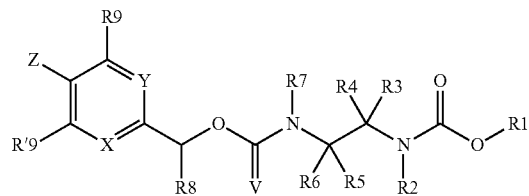

in which:
R1 is such that HOR1, obtained after the cleavage of the —C(O)—OR1 bond present in the formula (I) belong to the class of fluorophores leading to an intramolecular proton transfer in an excited state, called ESIPT,
R2, R3 and R4 are defined as follows:
either R2 is an (C1-C4) alkyl, R3 is an (C1-C4) alkyl or a hydrogen atom, and R4 is an (C1-C4) alkyl,
or R3 is an (C1-C4) alkyl or a hydrogen atom and R2 and R4 are bonded together and form, with the carbon and nitrogen atoms to which they are bonded, an aliphatic heterocycle which can be substituted by a water-solubilizing group,
or R2 is an (C1-C4) alkyl and R3 and R4 are bonded together and form, with the carbon atom to which they are bonded, an aliphatic carbocycle,
R5 and R6 are identical or different and represent, independently of each other, a hydrogen atom, an (C1-C4) alkyl, or an (C5-C10) aryl,
R7 is a hydrogen atom, or a group chosen from among the (C1-C4) alkyle and (C1-C4) alkoxy,
R8 represents a hydrogen atom or an (C1-C10) alkyl group, substituted or non-substituted, or a D1-D2-D3 group with:
D1 representing a triazolyl or —CH2-triazolyl group,
D2 representing an (C1-C10) alkylene, (C1-C10) alkenylene or (C1-C10) alkynylene group, said groups possibly being interrupted by one or several heteroatoms chosen from among O or N, a divalent glycosyl group, a —O—(CHR—CHR'—O)n-group or —N—(CHR—CHR'—O), n being an integer between 1 to 20, R and R', identical or different, representing H or CH3, upon condition that R and R' are not simultaneously CH3, an amino acid or peptide, or a combination of these groups,
D3 representing a maleimidocaproyl motif, amino acid, peptide, folic acid, antibody or antibody fragment bonded to D2, by a carboxylic acid function comprised in it, forming an ester or amide bond,
R9 and R'9, identical or different, represent a hydrogen atom, or an electron-withdrawing group such as a halogen atom, or a group chosen from among —NO2, —CN or —NH—C(O)—CH2-Ab with Ab representing an antibody,
V represents an oxygen atom or a sulfur atom,
X, Y and Z are such that:
either X represents CR10, Y represents CR'10 and Z represents OR0,
or X represents CR10, Y represents CR'10 and Z represents OR0,
or X represents CR10, Y represents a nitrogen atom and Z represents OR0,
or X represents a nitrogen atom, Y represents COR0 and Z represents R10 with:

R0 representing a glycosyl group bonded by its anomeric carbon atom to the rest of the molecule of formula (I), and R10 and R'10, identical or different, representing a hydrogen atom or an electron-donating group such as an (C1-C20) alkyl, an (C5-C24) aryl, or an (C1-C20) alkoxy, in the form of a mixture of optical isomers according to all proportions, or in an optical isomer enriched form.

The compounds (I) according to the invention, as a function of the selected glycosyl group, act as a molecular probe capable of revealing the presence of a specific glycosidase enzymatic activity by detection of fluorescence. The R0-O bond present in the compounds of the formula (I) is capable of cleavage, by hydrolysis, in the presence of a targeted glycosidase enzyme acting as a cleavage reaction catalyst. More specifically, the probe is invisible before encountering the targeted glycosidase enzyme, (namely, a "stealth probe"), but when it is chemically modified by said enzyme, it fragments via a cascade reaction to produce intense fluorescence. The probe is comprised of 4 molecular components: i) a tandem of auto-folding spacers which bear, at one end, ii) a glycosyl group playing the role of substrate for the target enzyme and, at the other iii) an OR1 group which, when released in its hydroxylated form HOR1 by said fragmentation, in an aqueous medium, belongs to the class of ESIPT fluorophores.

The pair of spacers comprises an eliminating type spacer and a cyclizing type spacer pre-organized for a cyclization. This specific choice of pair of spacers makes it possible to obtain two essential properties for the corresponding molecular probe: (a) it makes it insensitive to spontaneous deterioration and therefore to the production of a false positive fluorescent signal, and (b) it ensures rapid fragmentation kinetics during processing by the target enzyme for results adapted to applications in the field of life sciences. The R0 group can be cleaved from the rest of the molecule by the action of the target glycosidase, which leads to an unstable intermediate which auto-immolates via elimination reactions and cyclization/cleavage reactions, spontaneously and rapidly, to release a fluorescent precipitate and to thus produce a fluorescent signal. This unique molecular architecture makes possible an especially rapid enzymatic response, and specifically much more rapid than that obtained by the used of the probe described in document WO 2014/020285.

This invention therefore concerns the compounds of formula (I), regardless of their implemented variant described in this patent application, for the detection, in vivo, in human beings, of a glycosidase. The compounds of formula (I) according to the invention may also be used to detect a glycosidase, in vivo, in animals.

According to another embodiment, the invention concerns a method for detecting, in vitro or ex vivo, the presence of a glycosidase by means of the compound (I) according to the invention. More specifically, the invention concerns a method for detecting, in vitro or ex vivo, the presence of a glycosidase comprising the steps of:
- putting a sample thought to contain said glycosidase into contact with a compound (I) according to the invention,
- application of conditions suitable to enable the formation of a fluorescent compound, specifically in the form of a precipitate, by cleavage of the covalent bond between O and R0, followed by cleavage of the —C(O)—OR1 bond, after the elimination and cyclization reactions of the pair of spacers leading to the release of HOR1, and
- quantitative or qualitative analysis of said fluorescent precipitate.

The precipitate which can be obtained using the compounds of formula (I) according to the invention, by cleavage of the covalent bond between 0 and R0, followed by a cleavage of the —C(O)—OR1 bond, after an elimination and cyclization of the pair of spacers, is strongly fluorescent, while the compound of corresponding formula (I) is mildly fluorescent or not fluorescent at all. The compounds according to the invention, which are glycosidase enzyme substrates, behave like probes operating according to the on/off mode.

In particular, the detection method according to the invention can be implemented in physiological conditions, specifically in an aqueous medium buffered to a pH on the order of 7.4.

The invention also concerns the compounds of formula (II), intermediates in the synthesis of the compounds of formula (I):

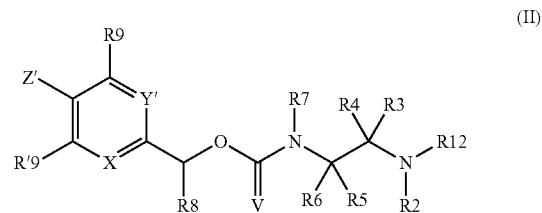

in which:
R2, R3, R4, R5, R6, R7, R8, R9, R'9 and V are as defined for the compounds of Formula (I),
R12 represents a hydrogen atom, or an amine functions protecting group, X, Y and Z are such that:
either X represents CR10, Y represents CR'10 and Z represents OR'0,
or X represents CR10, Y represents COR'0 and Z represents R'10,
or X represents CR10, Y represents a nitrogen atom and Z' represents OR'0,
Or X represents a nitrogen atom, Y' represents COR'0 and Z' represent R10 with R'0 representing a R0 group for which all alcohol functions are protected by a protecting group, and R0, R10 and R'10 are as defined for the compounds of formula (I), in the form of a mixture of optical isomers according to all proportions, or in an optical isomer enriched form.

The invention also concerns a method for the preparation of a compound (I) comprising the following steps:
Availability of a compound (II) as defined in the context of the invention,
Availability of a compound (III) of formula

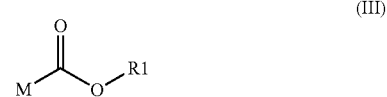

with R1 as defined for the compounds of formula (I) and M representing a leaving group, specifically a halogen atom, and in particular, a chlorine atom, an imidazolyl group or a para-nitro phenoxy, and preferably with M representing a chlorine atom.

obtaining the compound (IV) by addition reaction of said compound (III), said compound (IV) having the formula:

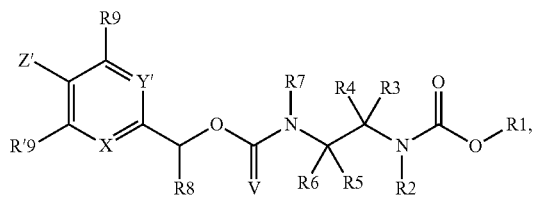

(IV)

in which R1, R2, R3, R4, R5, R6, R7, R8, R9, R'9, V, X, Y' and Z' are as defined for the compounds of formula (I) and (II), and deprotecting the alcohol functions present in the R'0 group of said compounds (IV) in order to obtain their compound (I).

The different compounds according to the invention can be found in all possible optical isomer forms, possibly in mixture according to all proportions, at least if not otherwise specified. According to a specific embodiment, the compounds according to the invention comprising an asymmetric carbon atom are found in a racemic form, with the R and S forms being found in almost equal proportions. According to another embodiment, the formula (I) compounds of the invention can be found in an enriched form in a diastereomer or enantiomer, with a diastereomeric or enantiomeric excess greater than 80%, or even greater than 95%, or in pure isomeric form, namely with a diastereomeric or enantiomeric excess greater than 99%.

The compounds are isolated in an enriched form in a diastereomer or enantiomer by classic separation techniques: for example, fractional recrystallizations of a racemic salt with an optically active acid or base for which the principle is well-known or, most often, classic chromatography techniques on the chiral or non-chiral phase.

If applicable, when compounds according to the invention comprise salifiable functions, they can be found in the form of a salt, specifically a hydrochloride or a trifluoroacetate. The invention will be described in a more detailed manner. First, certain terms used will be defined.

Definitions

By "aliphatic heterocycle", in the context of this invention, is understood a saturated cycle, substituted or not substituted, comprising 3 to 20 members, preferably 5 to 10 members, and more preferably, still, 5, 6, 7 or 8 members, and comprising at least one hetero-atom, such as O, N, or S.

By "aliphatic carbocycle", in the context of this invention, is understood a saturated cycle, substituted or not substituted, comprising 3 to 30 members, preferably 5 to 10 members, and more preferably still, 5, 6, 7 or 8 members constituted exclusively by carbon atoms.

By "alkyl", in the context of this invention, is understood a saturated hydrocarbon chain which can be linear or branched. Preferably, the term alkyl designates, at least if not otherwise specified, an alkyl group comprising 1 to 12 carbon atoms and, preferably 1 to 6 carbon atoms, and specifically an alkyl (C1-C4) group. Methyl, ethyl, n-propyl, isopropyl, and tert-butyl are examples of (C1-C4) alkyl groups (alkyl with 1 to 4 carbon atoms).

By "alkylene" is understood a divalent alkyl group.

By "aryl" is understood a mono- bi- or polycyclic ring, unsaturated hydrocarbon comprising, at least if not otherwise specified, from 5 to 24 members, from 5 to 20 members, preferably from alternating simple bonds and double bonds, 5 to 15 members, and comprising at least one aromatic ring As an example of any aryl group, we can cite the phenyl, naphtyl, anthracenyl, phenanthrenyl and cinnamyl groups. The term aryl also includes such mono-, bi- or polycyclic, unsaturated, hydrocarbon rings for which one of the constituting carbons is found in the —C(O) carboxy form, such as the 1H-phenalene-1-one (CAS no. 548-39-0).

By "arylene" is understood a divalent aryl group.

By "hetero-aryl" is understood a mono-, bi- or polycyclic carbocyclic ring, comprising, at least unless otherwise specified, from 5 to 24 members, preferably from 6 to 20 members, more preferably from 6 to 15 members, and comprising at least one aromatic group and at least one hetero-atom, chosen from among the atoms of oxygen, nitrogen or sulfur, integrated into the carbocyclic ring. By way of example of a hetero-aryl group, we may cite the 2-, 3- or 4-pyrininyl, 2- or 3-furoyl, 2- or 3-thiophenyl, pyrrolyl, imidazolyl, pyrazolyl, thiazolyl, bensothiazolyl, oxazolyl, benzoxazolyl, isoxazolyl, pyridinyl, pyrazinyl, pyrimidinyl, tetrazolyl, thiadazolyl, oxadiazolyl, triazolyl, pyridazinyl, indolyl, oxanyl, 4(1H)-quinolinonyl, dibenzothiophenyl, dibenzofuranyl and 9H-carbazolyl. The term heteroaryl also includes said groups for which one of the constituting carbon atoms is found in the carboxy —C(O)— form, such as 4(3H)-pyrimidinonyl or 4(3H)-quinazolinonyl.

When it is stated that a group is substituted without further specification, this means that it is substituted by one or several substitutes, specifically chosen from among the atoms of chlorine, bromine, iodine or fluorine, the cyano, alkyl, trifluoralkyl, trifluoromethyl, alcenyl, alcynyl, cycloalkyl, aryl, hetero-aryl, heterocyclico-alkyl, amino, alkylamino, diaklyamino, hydroxy, alcoxy, aryloxy, alcoxycarbonyl, aryloxycarbonyl groups, said groups themselves being able to be substituted. The terms used for the definition of these substitutes are those usually recognized by the person skilled in the art.

By "alkoxy" and "aryloxy", are respectively understood an —O-alkyl and —O-aryl group, with alkyl and aryl as defined in the context of this invention.

By "haloalkyl" is understood a saturated, linear or branched hydrocarbon chain in which at least one hydrogen atom has been replaced by a halogen atom.

By "glycosidase" is understood a hydrolase, glycoside enzyme which has the capacity to catalyze the hydrolysis of glycosidic bonds, so as to release at least one osidic compound.

By "glycosyl" group is understood any mono- or polysaccharide sugar bound to the rest of the molecule by a glycosyl bond, that is, via its anomeric carbon. The anomeric carbon may adopt the alpha or beta configuration. By way of example of glycosyl group, we can cite the mono-glycosyl groups, namely, formed by a single saccharide unit, and poly-glycosyl, namely, formed by several, identical or different, saccharide units. The saccharide units can specifically be of the hexose or pentose type, and chosen from among galactose, glucose, mannose, gulose, allose, altrose, idose, talose, fucose, fructose, arabinose, lyxose, ribose and xylose, for example. The saccharide units may be of L or D stereo chemistry.

Classically, the term "alkenyl" designates a hydrocarbon chain, linear or branched, comprising at least one double carbon-carbon bond, and presenting, unless it is otherwise specified, from 2 to 20 carbon atoms, and preferably from 2 to 6 carbon atoms.

In the context of this invention, the term "alkenylene" designates a divalent alkenyl group.

The term "alkynyl" designates a hydrocarbon chain, linear or branched, comprising at least one triple carbon-carbon bond, and presenting, unless it is otherwise specified, from 2 to 12 carbon atoms, and preferably from 2 to 6 carbon atoms.

By "alkynylene" is understood a divalent alkynyl group.

By "water-solubilizing group" is understood a hydrophilic group which makes it possible to improve the solubility of the probe in an aqueous medium, in relation, specifically, to a probe that only differs from it by the replacement of a water-solubilizing group by a hydrogen atom.

"Fluorescence" is the property by which a molecule that is excited by light of a given wavelength emits light of a longer wavelength. Fluorescence is a phenomenon that results from the interaction of a fluorophore with an incident photon. This process is also called excitation. The absorption of the photon results in an electron in the fluorophore to go from its basic state to a higher energy level. Then, the electron returns to its original level by emitting a photon. This process is called fluorescence emission. The fluorophore then emits light of a longer wavelength than that of the absorbed photon. This is due simply to the fact that the energy of the emitted photon is less than that of the absorbed photon, due to the dissipation of energy during the life span of the excited state. This is the definition given in patent application WO 2004/058787.

The compounds (I) according to the invention are called "glycosidase substrate" because they are transformed into another substance during a chemical reaction, in particular, a hydrolysis, catalyzed by a glycosidase. During such a reaction in an aqueous medium, the compounds (I) (also called "probe") are cleaved under the action of the target glycosidase, which leads to the formation of a fluorescent precipitate and of a non-fluorescent product.

The "pair of spacers" in the context of this invention is the fragment of the compound (I) which bears, at one end, a glycosyl-R0 group and, at the other end, an —OR1 group which, once released by hydrolysis, belong to the ESIPT class of fluorophores. This pair of spacers is comprised of a first spacer of eliminating type (which will undergo an elimination reaction following the hydrolysis that releases R0), and a second cycling type spacer (which will cyclize, following the elimination of the eliminating type spacer, thus making it possible to generate HOR1). FIG. 1 represents the degradation mechanism, using formula (I) compounds, calling on the pair of spacers according to the invention.

Compounds of Formula (I)

This invention concerns the compounds of the formula (I):

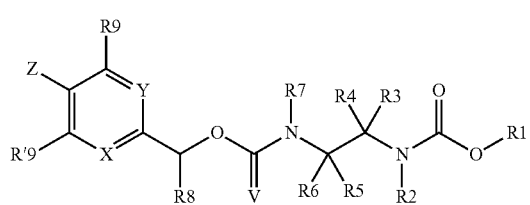

(I)

in which:
R1 is such that HOR1, obtained after the cleavage of the —C(O)-OR1 bond present in formula (1) belong to the class of fluorophores leading to an intra-molecular proton transfer in an excited state called ESIPT.

R2, R3 and R4 are defined as follows:
either R2 is an (C1-C4) alkyl, R3 is an (C1-C4) alkyl or a hydrogen atom, and R4 is an (C1-C4) alkyl,
or R3 is an (C1-C4) alkyl or a hydrogen atom and R2 and R4 are bonded together and form, with the carbon and nitrogen atoms to which they are bonded, an aliphatic heterocycle which can be substituted by a water-solubilizing group
or R2 is a (C1-C4) alkyl and R3 and R4 are bonded to each other and form, with the carbon atom to which they are bound, an aliphatic carbocycle.

R5 and R6 are identical or different and represent, independently of each other, a hydrogen atom, an (C1-C4) alkyl, or an (C5-C10) aryl, R7 is a hydrogen atom, or a group chosen from among the (C1-C4) alkyle and (C1-C4) alkoxy, R8 represents a hydrogen atom or an (C1-C10) alkyl group, substituted or non-substituted, or a D1-D2-D3 group with:
D1 representing a triazolyl or —CH2-triazolyl group,
D2 representing an (C1-C10) alkylene, (C1-C10) alkenylene or (C1-C10) alkynylene group, said groups possibly being interrupted by one or more heteroatoms chosen from among O or N, a divalent glycosyl group, an —O—(CHR—CHR')n-group or —N—(CHR—CHR'—O)n- with n being an integer varying from 1 to 20, R and R', identical or different, representing H or CH3 upon condition that R and R' are not simultaneously CH3, an amino acid or a peptide, or a combination of these groups,
D3 representing a maleimidocaproyl motif, amino acid, peptide, folic acid, antibody or antibody fragment bonded to D2, by a carboxylic acid function comprised in it, forming an ester or amide bond, R9 and R'9, identical or different, represent a hydrogen atom, or an electron-withdrawing group, such as a halogen atom, or a group chosen from among —NOS, —CN or —NH—C(O)—CH2-Ab with Ab representing an antibody, V represents an oxygen atom or a sulfur atom, X, Y and Z are such that:
either X represents CR10, Y represents CR'10 and Z represents OR0,
or X represents CR10, Y represents CORO and Z represents R'10
or X represents CR10, Y represents a nitrogen atom and Z represents OR0,
or X represents a nitrogen atom, Y represents CORO and Z represents R10 with:
R0 representing a glycosyl group bound by its anomeric carbon atom to the rest of the molecule of formula (I), and
R10 and R'10, identical or different, representing a hydrogen atom or an electron-donating group such as an (C1-C20) alkyl, an (C5-C24) aryl, or an (C1-C20) alkoxy, in the form of a mixture of optical isomers according to all proportions, or in an optical isomer enriched form.

The OR1 group is selected so that the obtained fluorescent precipitate which corresponds to R1OH, released after cleavage of the —C(O)—OR1 bond, is an ESIPT fluorophore.

Preferably, R1 is an aromatic group comprising one or more aromatic rings, substituted or non-substituted, said rings being able to comprise one or more hetero-atoms chosen from among the nitrogen, oxygen or sulfur atoms and/or one or more carbon atoms in the form of a C=O carbonyl.

Examples of such OR1 groups respond to the formula (A1):

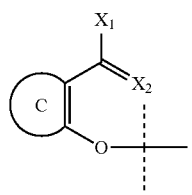

(A1)

in which:
either X2 is an oxygen atom and X1 is a —NHO, —OH, —SH, (C1-C20)alkyl, (C5-C24)aryl, —O—(C1-C20)alkyl, —O-phenyl, —NH—(C1-C20)alkyl or —NH-phenyl, —S—(C1-C20)alkyl or —S—(C5-C24)aryl group, said alkyl and phenyl groups being able to be substituted or non-substituted,
or X2 represents a nitrogen atom and is bound to X1 which then represents CH, O, S, N or NH to form a (C5-C24) hetero-aryl, substituted or non-substituted,

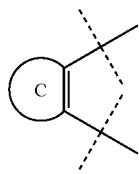

represents an (C5-C24) aryl or a (C5-C24) hetero-aryl, substituted or non-substituted, for example, chosen from among the phenyl, naphtyl groups, and:

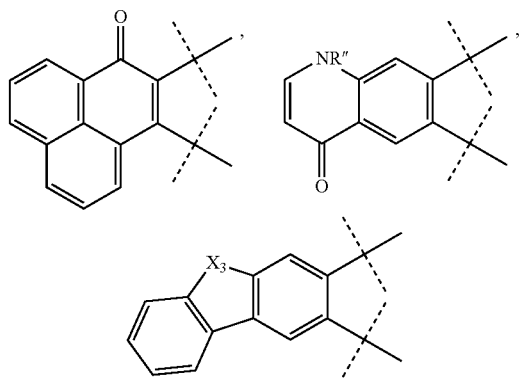

said groups being able to be substituted or non-substituted, with X3 which represents S, O or NRd and Rd which represents a hydrogen atom or an (C1-C4) alkyl group.

The ESIPT fluorophores show a Stokes shift which exceeds 100 nm and often approach 200 nm. All ESIPT fluorophores lose this emission of fluorescence corresponding to a Stokes shift greater than 100 nm, if their OH group of the phenolic type gives rise to the intra-molecular transfer of a proton in the excited state, is alkylated, acylated or otherwise functionalized. This functionalization prevents the transfer of a hydrogen atom to an X2 hetero-atom in the illustration provided with formula (A1), during excitation by irradiation, and thus prevents the emission of fluorescence characteristic of the proton transfer method.

The incorporation of the HOR1 hydroxyl into the carbamate group of the formula (I) compound prevents the proton transfer. The intra-molecular proton transfer may then occur using the hydroxy group obtained following the scission of the —C(O)—OR1 bond.

Most often, the R1 group corresponds to a phenyl group which is non-substituted or substituted and/or which is merged with one or more unsaturated carbocycles, possibly comprising a hetero-atom such as nitrogen. This OR1 phenoxy derivative, when it is not bonded to the substrate, corresponds in its protonated form to an HO—R1 phenolic derivative which belongs to the ESIPT class of fluorophores.

Some —OR1 derivatives correspond, for example, to one of the following preferred structures (A2) or (A3):

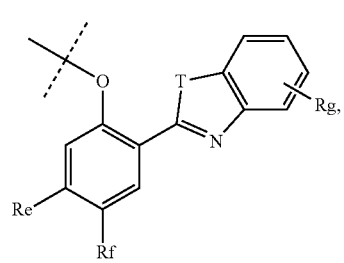

(A2)

T is —NH—C(O)—, —S—, —O—, —NH—, —N((C1-C20)alkyl)- or —N((C5-C24)aryl)-,
Re is a hydrogen atom or an electron-withdrawing carbon substitute such as —CN or —COORh, with Rh which represents an (C1-C4) alkyl group, or Re is —CON-RiRj, with Ri and Rj, identical or different, which represent a hydrogen atom, or an (C1-C4) alkyl group, or Re is —CF3, or a 2-oxazolyl, 2-thiazolyl, 2-imidazolyl, 2-benzoiumidazolyl, 4-pyrimidinone-2-yl or quinazolinone-2-yl group,
Rf is a hydrogen atom, a chlorine, bromine, iodine or fluorine atom, —OH, —NH2, —NRkRl, —NHRk or —ORk, with Rk and Rl, identical or different, which each, independently, represent an (C1-C4) alkyl group.
Or Re and Rf are bonded to each other to form a hydrocarbon chain comprising 4 or 5 members, saturated or unsaturated, substituted or non-substituted, possibly interrupted by one or more hetero-atoms chosen from among N, S and O,
Rg is a hydrogen, Br, Cl, I or F atom,

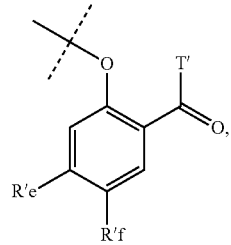

(A3)

in which:
  T' is —NH2, —OH, an (C5-C24) aryl group, an (C1-C4) alkyl group, —SH, —NHR'g, —OR'g, —NR'gRh' or —SR'g, R'g and Rh', identical or different, represent an (C1-C4) alkyl or aryl group.
  R'e is a hydrogen atom or an electron-withdrawing carbon substitute such as —CN or —COOR'i, with R'i which represents an (C1-C4) alkyl group, or R'e is —CONRjR'k, with R'j and R'k, identical or different, which represent a hydrogen atom or an (C1-C4) alkyl group, or R'e is —CF3, or a 2-oxazolyl, 2-thiazolyl, 2-imidazolyl, 2-benzimidazolyl, 4-pyrimidionon-2-yl or quinazolinon-2-yl group,
  R'f is a hydrogen, chlorine, bromine, iodine or fluoride atom, —OH, —NH2, —NR'lR'm or —OR'l, with R'l and R'm, identical or different, which represent an (C1-C4) alkyl group.
  or R'e and R'f are bonded to each other to form a hydrocarbon chain comprising 4 or 5 members, saturated or unsaturated, substituted or non-substituted, possibly interrupted by one or more hetero-atoms chosen from among N, S and O. We may specifically refer to applications WO 2013/045854, WO 2014/020285 and WO 2015/197981 which give examples of such ESIPT fluorophores which can be used in this invention.

According to a specific embodiment of the invention, R1 is an aromatic group with —OR1 which responds to one of the following formulas, (A4) or (A5):

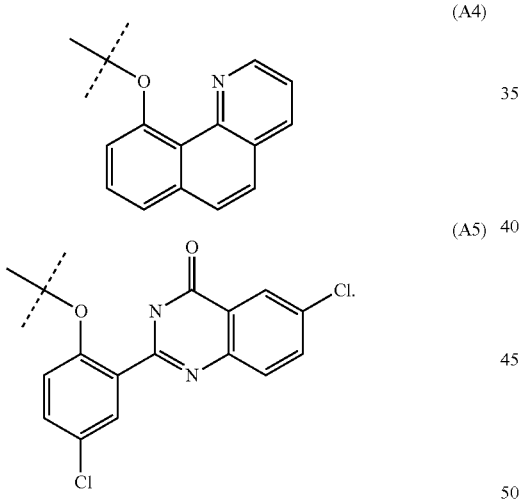

The very large Stokes shift of such fluorophores (approximately 170 nm for A5) or of any analog of the HPQ will contribute to the excellent sensitivity of the probe and render the released fluorophore easily distinguishable from the native fluorescence which may come from the biological sample on which the analysis will be conducted. According to one embodiment of the invention, R2 is an (C1-C4) alkyl, R3 is an (C1-C4) alkyl or a hydrogen atom, and R4 is an (C1-C4) alkyl. According to another specific embodiment, R2, R3 and R4, identical or different, represent an (C1-C4) alkyl group, for example, methyl or ethyl. According to a specific embodiment, R2=R3=R4=—CH3.

According to another embodiment, or R3 is an (C1-C4) alkyl or a hydrogen atom and R2 and R4 are bonded together and form, with the carbon and nitrogen atoms to which they are bonded, an aliphatic heterocycle which can be substituted by a water-solubilizing group. According to an embodiment, R3 is a hydrogen atom or an (C1-C4) alkyl, preferably a hydrogen atom, and R2 and R4 are bonded to each other and form a —(CH2)m- chain with m=3, 4 or 5. According to another embodiment, R3 is a hydrogen atom or an (C1-C4) alkyl group, preferably a hydrogen atom, and R2 and R4 are bonded to each other and form a —CH2CH2-NR11-CH2- chain in direction of R2 toward R4, R11 representing a hydrogen atom or -(L)n-GP with n which is equal to 0 or 1, L a linking arm and GP a water-solubilizing group, i.e. the compound (I) then has the formula:

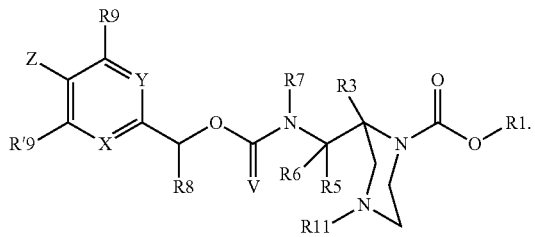

Very often, for synthesis purposes, n=1 and L is a linking arm and, specifically, a -(L1)m1-(L2)m2-(L'1)m'1- arm (in the piperazine direction→GP group) with:
  L1 and L'1, identical or different, which are chosen from among —O—, —NH—, —N(C1-C6) alkyl)-, —N(phenyl)-, —N(aryl)-, —C(O)—, —C(O)O—, —OC(O)—, —OC(O)—O—, —NHC(O)—O—, —OC(0)-NH—, —NHC(O)—NH—, —S—, —SOC—, —N═N—, —NHC(O)— and —CONH—;
  L2 which is chosen from among the following divalent groups: (C1-C20)alkylene, (C1-C20)alkenylene, (C1-C20)alkynylene, (C6-C24)arylene, (C7-C44)alkylarylene, (C7-C44)alkenylarylene, (C7-C44)alkynylarylene, (C7-C44) alkylcycloalkylene, (C7-C44) alkenylcycloalkylene, (C7-C44)alkynylcycloalkylene (C7-C44)alkylheterocycloalkylene, (C7-C44)alkenylheterocycloalkylene, (C7-C44)alkynylheterocycloalkylene; said groups being possibly interrupted or terminated by a triazole group, and being able to be substituted or non-substituted, specifically by one or more substitutes chosen from among the (C1-C10) alkoxy, (C1-C10)alkyl, (C6-C10)aryl, amide, imide, phosphide, nitride, (C1-C10)alkenyl, (C1-C10) alkynyl and —OH; and
  m1, m'1 and m2, identical or different, which are equal to 0 or 1.

The L arm, when present, will be chosen to extend the GP group from piperazine or for synthesis reasons. According to one preferred embodiment, L represents-(L1)m1-(L2)m2-(L'1)m'1 with L1=—C(O)—, m1=m2=1, m'1=1 or 0 and L2 and L'1 as defined above, and, specifically, L represents —C(O)—(CH2)p-L3- with p which is equal to 1, 2, 3 or 4 and L3 which is a triazole group and specifically a 1H-1,2,3-triazole group.

GP is a water-solubilizing group. As an example of a water-solubilizing group, we cite the groups that can form a charged species in aqueous solution. As an example of water-solubilizing GP group, we cite the F1 functions chosen from among the amines (primary, secondary or tertiary), amidine, guanidine or tetrazole; the F2 cationic or anionic functions, and specifically the ammonium, carboxylate, sulfonate or phosphate type groups; the groups comprise one or more of these F1 and/or F2 functions; the polyethylene glycols; the sugars or polysaccharides such as glucose, galactose and mannose; the peptide groups such as poly-lysine, poly-arginine, the TAT-peptides. As an example of amine functions, we cite —NH2, —NH(C1-C4) alkyl, and the dialcylamines in which the alkyl groups are identical or different and comprise 1 to 4 atoms of carbon.

According to another embodiment, R2 is an (C1-C4) alkyl and R3 and R4 are bonded together and form with the carbon atom to which they are bound, an aliphatic carbocyclic ring, preferably a cyclohexyl.

These two ways of pre-organizing the spacer for cycliza-tion, consisting either of introducing two alkyl substitutes (or forming a carbocyclic ring) on the alpha carbon of the —N—C(V)—O— group, or of including the bond between the group nitrogen —N—C(V)—O— and its alpha carbon in a heterocyclic ring, accelerate the immolation process.

According to one embodiment, R5 and R6 are identical and represent a hydrogen atom. According to one embodi-ment, R7 represents a hydrogen atom or an (C1-C4) alyl group such as a methyl, and preferably a hydrogen atom.

According to one embodiment, R5, R6 and R7 each represent a hydrogen atom.

According to one embodiment, R8 a hydrogen atom.

According to another embodiment, R8 is a -D1-D2-D3 group, with D1, D2 and D3 as defined in the context of this invention. According to this embodiment, D3 can specifi-cally represent a folic acid motif, antibody or peptide, which are groups targeting a cellular receptor, in order to improve the selectivity of the compounds of formula (I) for certain specific cells.

According to a specific embodiment of the invention, R8 is a -D1-D2-D3 group, with D1 representing a —CH2-triazolyle group, D2 representing an (C1-C10) alkylene group, preferably interrupted by one or more hetero-atoms chosen from among O or N, preferably 0, and D3 repre-senting a maleimidocaproyl motif, amino acid, peptide, folic acid, antibody or antibody fragment, preferably folic acid, bonded to D2 by a carboxylic acid function so as to form an amide or ester bond, preferably an amide function. Accord-ing to a specific embodiment, R8 is a -D1- D2-D3 group with the following formula:

play the role of catalyst. This is because said glycosidase enzyme is called catalytically active.

R0 represents a glycosyl group bonded by its anomeric carbon atom to the rest of the molecule. R0 can be cleaved from the rest of the compound of formula (I) by the catalytic action of a glycosidase enzyme, in particular in an aqueous medium. As examples of glycosidase enzymes which can be targeted by fluorescent probes according to the invention, we cite N-acetyl-β-galactosaminidase; N-acetyl-β-glucosamini-dase; α-amylase; α-arabinofuranosidase, α-arabinosidase; β-cellobiosidase; β-chitobiosidase; α-galactosidase; β-ga-lactosidase; α-glucosidase; β-glucosidase; β-glucuronidase; α-maltosidase; α-mannosidase; β-mannosidase; β-xylosi-dase; β-D-fucosidase; α-L-fucosidase, β-L-fucosidase; L-iduronidase or cellulase (Orenga, S., James, A. L., Nanafi, N., Perry, 1. D., & Pincus, D. H. (2009). Enzymatic sub-strates in microbiology. Journal of Microbiological Meth-ods, 79(2), 139-155).

The R0 group will be, preferably, chosen so as to be specific for a glycosidase of interest. On the other hand, certain glycosidases are able to cleave a set of different R0 groups; among these, we cite hexosaminidase.

All possible glycosyl groups which correspond to an R0-O group that is cleavable in an aqueous medium in the presence of a glycosidase can be used as R0. Glycosyl units can be functionalized or not, specifically with an acetyl or amino group. The N-acetyl hexosamines are examples of glycosyl groups. Most often, the glycosyl group will com-prise 1 to 50 saccharide units. In the case of polyglycosyl, this may act as a homopolymer or a copolymer with a random, alternated or block structure.

Examples of such R0 groups are given below: the mono-glycosyl groups chosen from among galactosyl, glucosyl, mannosyl, gulosyl, allosyl, altrosyl, idosyl, talosyl, fucosyl, fructosyl, arabinosyl, lyxosyl, ribosyl, xylosyl, glucuronyl and N-acetyl-hexosaminyl and the polyglycosyl groups con-stituted of several of these monoglycosyl groups, identical or different.

According to one embodiment, R0 is a group that is cleavable under the action of a glycosidase, chosen from

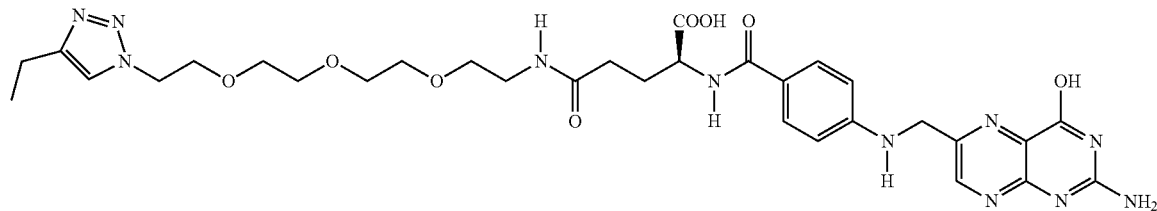 [SMILES: CCc1cn(CCOCCOCCOCCNC(=O)CC[C@H](NC(=O)c2ccc(NCc3cnc4nc(N)nc(O)c4n3)cc2)C(=O)O)nn1]

According to an embodiment, at least one of the R9 or R'9 groups represents a halogen atom, a —NO2 group or a —CN group, preferably an —NO2 group. According to a preferred embodiment, R9 represents a hydrogen atom and R'9 represents a halogen atom, a —NO2 group or a —CN group, preferably a —NO2 group.

According to one embodiment, R10 and, if applicable, R'10, represent a hydrogen atom. According to one embodi-ment, V represents an oxygen atom.

The R0 groups have the characteristic of being able to be cleaved from the rest of the molecule by the action of a glycosidase enzyme. The enzyme plays the role of catalyst in the scission between R0 and the oxygen atom to which it is bonded. Such a scission can be the result of hydrolysis in an aqueous medium for which the glycosidase enzyme will among N-acetyl-β-galactosaminidase; N-acetyl-β-glu-cosaminidase; α-amylase; α-arabinofuranosidase, α-arab-inosidase; β-cellobiosidase; β-chitobiosidase; α-galactosi-dase; β-galactosidase; α-glucosidase; β-glucosidase; β-glucuronidase; α-maltosidase; α-mannosidase; β-man-nosidase; β-xylosidase; β-D-fucosidase; α-L-fucosidase, β-L-fucosidase; L-iduronidase or cellulase; and R0 is a mono-glycosylated group bound by its anomeric carbon chosen from among galactosyl, glucosyl, mannosyl, gulosyl, allosyl, altrosyl, idosyl, talosyl, fucosyl, fructosyl, arabino-syl, lyxosyl, ribosyl, xylosyl, glucuronyl and N-acetyl-hexosaminyl or a polyglycosylated group constituted of several, for example 2 to 20, preferably from to 10, and more preferably from 2 to 6, of these monoglycosylated groups, identical or different.

According to one embodiment, R0 is a group that is cleavable by the action of a galactosidase, for example, a β-galactosidase, an induronidase, a glucosidase, an N-acetyl-D-glucosaminidase, an N-acetyl-D-galactosaminidase, a mannosidase, a fucosidase, a glucuronidase, specifically of a β-glucuronidase or of a cellulase; and R0 is a mono-glycosylated group, bound by its anomeric carbon, chosen from among the D-glucuronyl, L-iduronyl, the D-glucopyranosyl, D-galactopyranosyl, N-acetyl-D-glucosaminyl, N-acetyl-D-galactosaminyl, D-mannopyranosyl, L-fucopyranosyl or a polyglycosylated group constituted of several, for example, from 2 to 20, preferably from 2 to 10, and more preferably from 2 to 6 of these monoglycosylated groups, identical or different.

According to one embodiment, X, Y and Z are such that:

either X represents CR10, Y represents CR'10 and Z represents OR0, or X represents CR10, Y represents COR0 and Z represents R'10 with R10, R'10 and R0 as defined in the context of the invention.

In the context of this invention, we will use, in particular, the specific definitions of substitutes given in combination.

According to a first, specific embodiment, the compound (I) is as represented by formula (Ia) below, in the form of a mixture of optical isomers according to all proportions, or in an enriched form in an optical isomer, where R1, R2, R3, R4, R5, R6, R7, R8, R0 and V are as defined in the context of this invention.

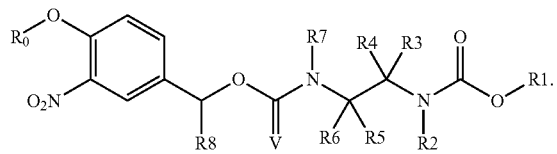

(Ia)

According to a second, specific embodiment, the compound (I) is as represented by formula (Ib) below, in the form of a mixture of optical isomers according to all proportions, or in an enriched form in an optical isomer, where R1, R2, R3, R4, R9, R'9, X, Y and Z are as defined in the context of this invention.

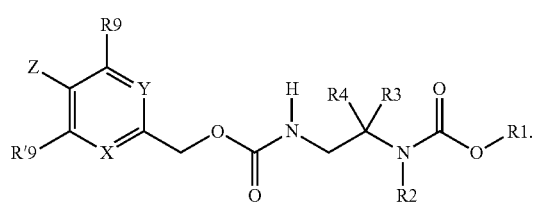

(Ib)

According to a third, embodiment, the compound (I) is as represented by formula (Ic) below, in the form of a mixture of optical isomers according to all proportions, or in an enriched form in an optical isomer, where R0 and R1 are as defined in the context of this invention.

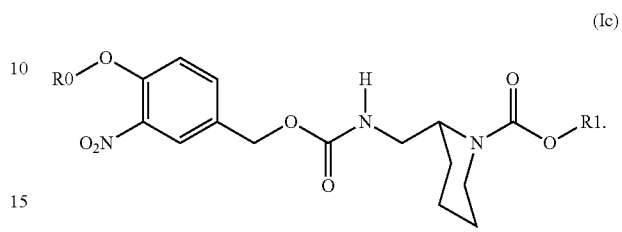

(Ic)

According to a fourth, embodiment, the compound (I) is as represented by formula (Id) below, in the form of a mixture of optical isomers according to all proportions, or in an enriched form in an optical isomer, where R1, R2, R3, R4, R9, R'9, D1, D2, D3, X, Y and Z are as defined in the context of this invention:

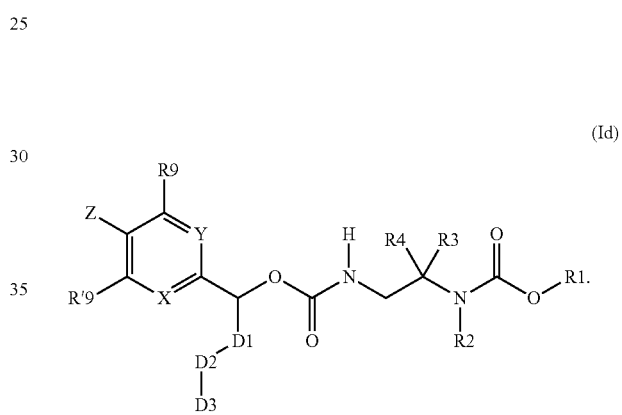

(Id)

According to a fifth embodiment, the compound (I) is as represented by formula (Ie) below, in the form of a mixture of optical isomers according to all proportions, or in an enriched form in an optical isomer, where R0, R1, D1, D2 and D3 are as defined in the context of this invention:

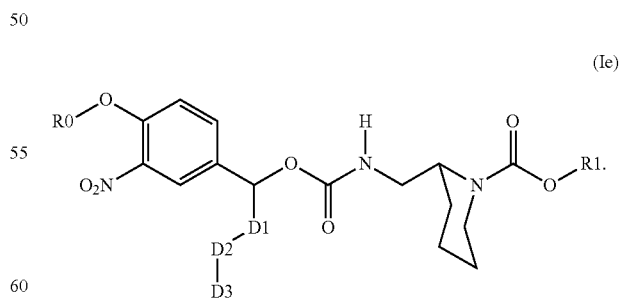

(Ie)

According to a specific embodiment, the compound (I) is as represented by formula (If) below, in the form of a mixture of optical isomers according to all proportions, or in an enriched form in an optical isomer, where R0 is as defined in the context of this invention:

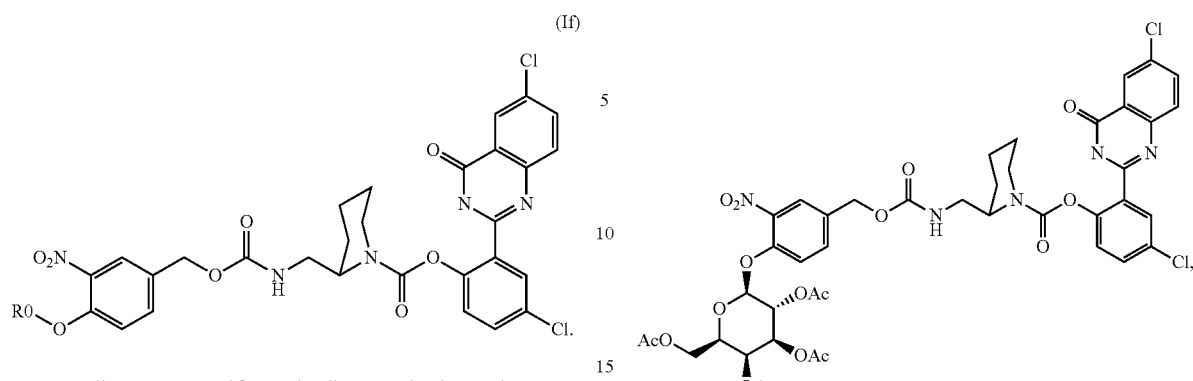
According to a specific embodiment, the invention concerns compounds, in the form of a mixture of optical isomers according to all proportions, or in an enriched form as an optical isomer, chosen from among:
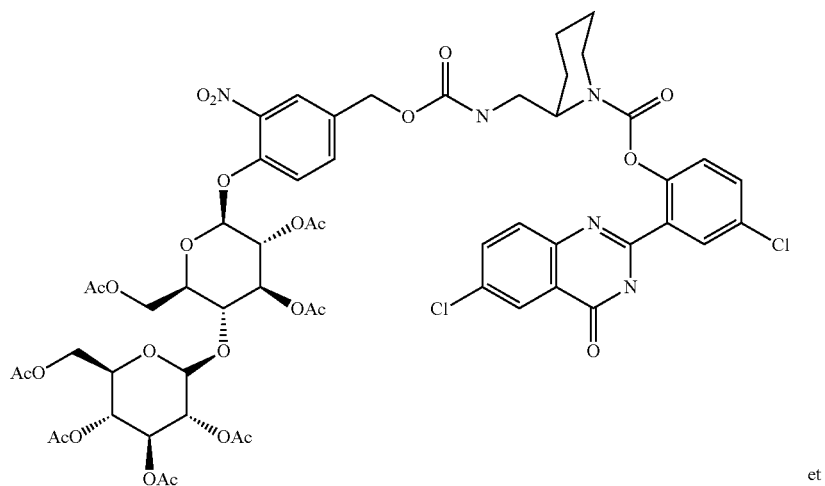
et
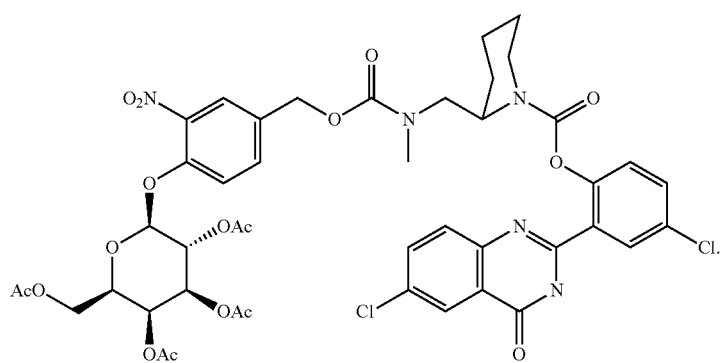

Compounds of Formula (II)

This invention also concerns the compounds of the formula (II):

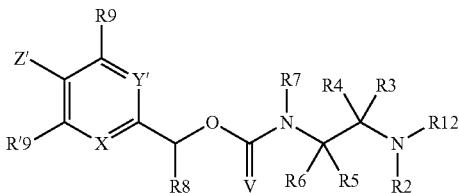

(II)

in which:
R2, R3, R4, R5, R6, R7, R8, R9, R'9 and V are as defined for the compounds of Formula (I),
R12 represents a hydrogen atom, or an amine functions protecting group,
X, Y and Z are such that:
either X represents CR10, Y represents CR'10 and Z represents OR'0,
or X represents CR10, Y represents COR'0 and Z represents R'10,
or X represents CR10, Y represents a nitrogen atom and Z' represents OR'0,
or X represents a nitrogen atom, Y represents COR'O and Z represents R10,
with R0' representing a nitrogen atom, for which all alcohol functions are protected by a protecting group, and R0, R10 and R'10 being as defined for the compounds of formula (I), in the form of a mixture of optical isomers according to all proportions, or in an optical isomer enriched form.

The compounds of formula (II) are synthesis intermediates of the compounds of formula (I), by amine functions protective group is understood protective groups such as those described in Protective Groups in Organic Synthesis, Greene T. W. et Wuts P. G. N., ed. John Wiley and Sons, 2006 and in Protective Groups, Kocienski P. J., 1994, Georg Thieme Verlag.

According to an embodiment, R12 is an amine functions protective group. As an example, R12 represents an amine function protective group chosen from among the allyl orcarbamate groups, such as a tert-butoxycarbonyl (Boc) group, fluorophenyl methoxycarbonyl (Fmoc) group, allyloxy carbonyl (Alloc) group or 2,2,2-trichloroethoxycarbonyl (Troc) group.

According to a specific embodiment, R12 represents a hydrogen atom.

According to an embodiment, R'0 represents an R0 group for which the alcohol functions are protected by an alcohol functions protective group, preferably under the reactional conditions used during the reaction between compounds (II) and (III), and specifically by silyl groups such as the trimethylsilyl groups tert-butyldiphenylsilyl and triiso-propylsilyl; in the form of acetal and specifically of 1,3-dioxolane; or in the form of fatty acids ester.

According to one embodiment, the compound (II) is as represented by formula (IIa) below, in the form of a mixture of optical isomers according to all proportions, or in an enriched form in an optical isomer, where R2, R3, R4, R5, R6, R7, R8, R12, R0 and V are as defined in the context of this invention.

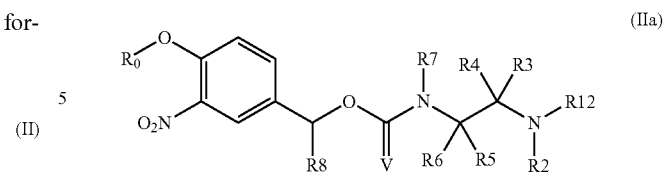

(IIa)

According to a second specific embodiment of the invention, the compound (II) is as represented by formula (IIb) below, in the form of a mixture of optical isomers according to all proportions, or in an enriched form in an optical isomer, where R2, R3, R4, R9, R'9, R12, X, Y and Z are as defined in the context of this invention.

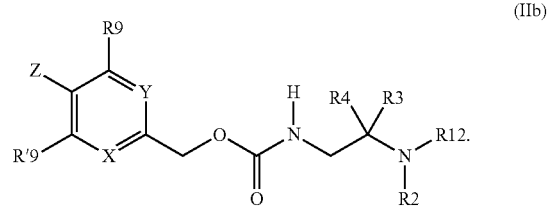

(IIb)

According to a third embodiment, the compound (II) is as represented by formula (IIc) below, in the form of a mixture of optical isomers according to all proportions, or in an enriched form in an optical isomer, where R0 and R12 are as defined in the context of this invention.

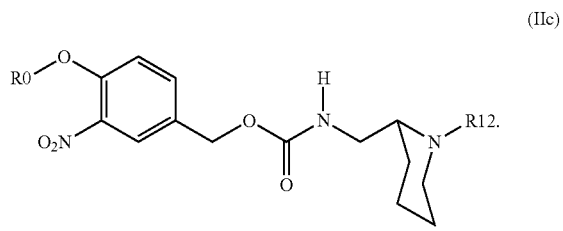

(IIc)

According to a fourth specific embodiment of the invention, the compound (II) is as represented by formula (IId) below, in the form of a mixture of optical isomers according to all proportions, or in an enriched form in an optical isomer, where R2, R3, R4, R9, R'9, R12, D1, D2, D3, X, Y and Z are as defined in the context of this invention.

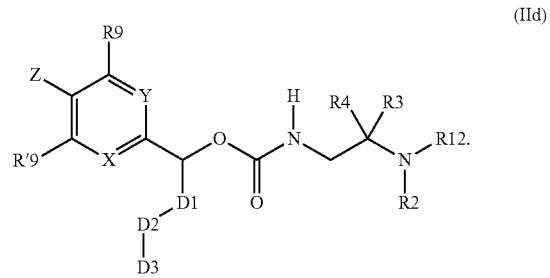

(IId)

According to a fifth embodiment, the compound (II) is as represented by formula (IIe) below, in the form of a mixture of optical isomers according to all proportions, or in an enriched form in an optical isomer, where R0, R12, D1, D2 and D3 are as defined in the context of this invention.

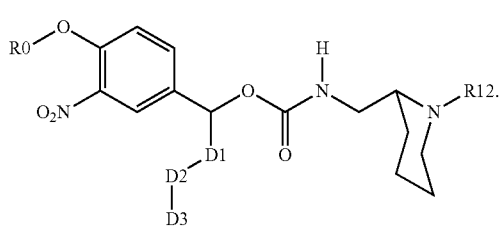
(IIe)

Method for the preparation of the compounds of formula (I) This invention also concerns a method for the preparation of a compound (I), as described in the context of this invention, comprising the following steps:

Availability of a compound (II) as defined in the context of the invention,

Availability of a compound (III) of formula

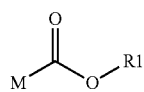
(III)

With R1 as defined for the compounds of formula (I) and M representing a group beginning, specifically, with a halogen atom and in particular, chlorine, an imidazolyl group or a para nitro phenoxy, and preferably with M representing a chlorine atom.

obtaining the compound (IV) by addition reaction of said compound (III), said compound (IV) having the formula:

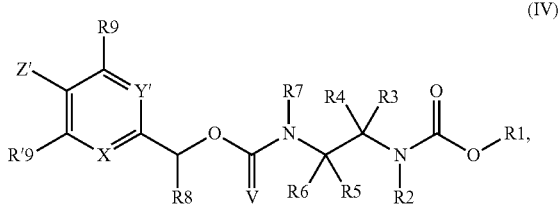
(IV)

In which R1, R2, R3, R4, R5, R6, R7, R8, R9, R'9, V, X, Y' and Z' are as defined for the compounds of formula (I) and (II), and deprotecting the alcohol functions present in the R'0 group of said compounds (IV) in order to obtain said compound (I).

According to one embodiment, the reaction of addition of compound (II) to compound (III) is executed with a compound (II) in which R12 is a hydrogen atom.

According to another embodiment, we have available a compound (II) in which R12 is not a hydrogen atom, and a step of deprotecting the amine function of the compound (II) is executed prior to the reaction of addition of compound (II) to compound (III) so as to obtain a compound (II) such as R12=H.

When V=O, compound (II) can be beneficially obtained according to the following steps:
Availability of a compound (V) of the following formula:

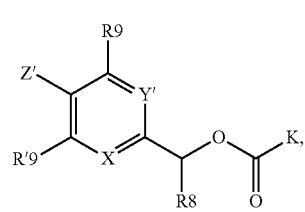
(V)

Availability of a compound (VI) of formula

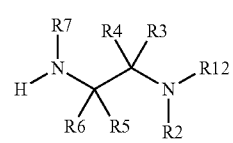
(VI)

and obtaining compound (II) by addition reaction of said compound (VI) to the compound (V),
in which R2 R2, R3, R4, R5, R6, R7, R8, R9, R'9, R12, V, X, Y' and Z' are as defined in the context of the invention, and K represents a leaving group, in particular a halogen, and specifically chlorine, or an imidazolyl or para-nitrophenyl group.

When R8=D1-D2-D3, R8 may be introduced by click chemistry. The formation of a triazole group may be executed by reaction between the —N3 and alkynyl functions, using techniques which are well-known to the person skilled in the art.

More specifically, when R8=D1-D2-D3 with D1 representing a —CH2-triazolyl group, D2 representing an (C1-C10) alkylene group, preferably interrupted by one or more hetero-atoms chosen from among O or N, preferably from 0, and D3 representing folic acid motif, bound to D2 by a carboxylic acid function comprised in it so as to form an amide bond, R8 may be introduced by reaction between an alkyne, borne by the precursor of formula (I), and an azide according to a Huisgens cyclo-addition reaction. Azide is formed prior to the reaction between the acid function of the folic acid and the amine function of a compound of formula H2N-D2-N3.

It is also possible, preferably, to use the methods illustrated in the examples.

Detection of the Presence of Glycosidase

The compounds of formula (I) according to the invention may also be used to detect a glycosidase, in vivo, in animals or in human beings.

The administration of the compound of formula (I) can be completed by an intravenous or intra-peritoneal injection, or cutaneously, by use of a spray containing the molecule in solution, for example.

Analysis of the fluorescence of the compound of formula (I) may take place in an imaging chamber using fluorescence or epi-fluorescence type tomography techniques. The invention also concerns a method for detecting, in vitro or ex vivo, the presence of a glycosidase by means of the compound (I) according to the invention. More specifically, the invention concerns a method for detecting, in vitro or ex vivo, the presence of a glycosidase, comprising the following steps of:

putting a sample thought to contain said glycosidase into contact with a compound (I) according to the invention, application of conditions suitable to enable the formation of a fluorescent compound, specifically in the form of a precipitate, by cleavage of the covalent bond between O and R0, followed by the cleavage of the —C(O)—OR1 bond, leading to the release of HOR1 and quantitative or qualitative analysis of said fluorescent precipitate.

The sample can be any suitable biological sample, from a human being, an animal, a plant or a micro-organism. In the case of a sample from a human being or an animal, this may specifically be a sample of a biological fluid, specifically a sample of whole blood, serum, plasma, urine, a tissue sample, or a sample of isolated cells, and in particular, of a cellular medium. In the case of a sample from a plant, this can be a plant extract, an extract of a fungus or of algae, of living cells, and in particular, of a cellular medium. It is also possible for the sample to directly comprise the plant. In the case of a sample from a micro-organism, the micro-organism can be a bacterium, a virus, a fungus or a yeast, and can also be a micro-biota. The sample may directly comprise the micro-organism, or and extract of the latter, or even the culture medium in which the micro-organism was incubated. In all cases, the sample can be used as is, or can be submitted, before being put in the presence of the probe, to an enriching or culturing type preparation, well known to the person skilled in the art.

In the case of a sample coming from an animal, a plant or a micro-organism, the invention concerns a method for detecting the presence of a catalytically active glycosidase comprising the steps of:

putting a sample thought to contain said glycosidase into contact with a compound (I) according to the invention, said, applying suitable conditions in order to make possible the formation of a fluorescent compound, specifically in the form of a precipitate, by cleavage of the covalent bond between O and R0, followed by a cleavage of the —C(O) OR1, bond, after the elimination and cyclization reactions of the pair of spacers, and quantitative or qualitative analysis of said fluorescent precipitate.

Analysis of the compound or fluorescent precipitate can comprise:

a step of exposing the fluorescent precipitate to a light source capable of producing light at an absorption wave length of the fluorescent precipitate, and a step of detecting the fluorescence of the resulting precipitate.

The analysis may also comprise a step, subsequent to the step of detection of the fluorescence, of sorting analyzed samples based on the signal provided by said fluorescent precipitate. The sorted samples can be colonies of microorganisms, separated in space, such as dishes of microbiological cultures. The sorted samples can also be small objects, liquids, solids, gelatinous or of heterogeneous composition, containing either bio-molecules or colonies of micro-organisms. When detection is done in parallel on several samples, the sorting can be done, for example, by diversion of a flow of samples set into motion in a device making it possible to sort according to an optical signal, representative of the emitted fluorescence, such as flow cytometry or a digital milli- or micro-fluid device.

This invention makes the activity of glycosidases accessible by fluorescent imaging using ESIPT fluorophores. Beneficially, no background noise due to spontaneous degradation (that is, in the absence of the target glycosidase, in a physiological medium) was observed. The probe itself is slightly fluorescent, or not at all fluorescent, in particular at the wavelength of emission of the ESIPT fluorophore fiber on which the detection/imaging instrument is set. Thus, the probe functions in an on/off mode and can be used for the development of analyses with maximum sensitivity. Depending on the R0 group chosen, this invention makes it possible to target glycosidases with high selectivity for specific glycosyl groups.

Probes according to the invention are interesting for several high sensitivity applications in the life sciences, specifically: (1) high yield targeting of glycosidase activity expressed by bacterial colonies on an agar plate (analysis of colonies); (2) the in vitro detection of glycosidase in biological liquids (hematology and others); (3) visualization of a glycosidase activity at the level of a simple cell in flow cytometry; (4) the detection of sub-cellular glycosidases in cultivated cells (confocal fluorescence microscopy); (5) the histo-chemical detection of glycosidase (at the tissue level); and finally (6), in vivo imagery of an entire animal.

Thus, the compounds of formula (I), as glycosidase substrates according to this invention, have a large number of potential applications. Examples of these applications include the design of analyses of bacterial colonies. These are currently executed on an agar dish (Petri dish) where up to 3,000 colonies can be distinguished without having to actively separate them into separate compartments such as the wells contained in a multi-well dish. Thus, it is possible to (1) design tests on clinical samples making it possible to identify from among a group of bacterial lines a pathogenic line of interest and (2) to complete large-scale parallel tests of a bank of self-produced proteins expressed by a classic bacterial host (often commercial). This collection of proteins can be understood to contain a protein of specific interest, for example, a glycosidase with a selectivity for a specific glycosyl group, or a glycosidase hydrolyzing a non-natural glycosidic bond. In the field of directed evolution of glycosidases or enzymes in particular, there is high demand for effective and sensitive analyses for sieving very large numbers of protein variants, easily exceeding $10^6$. The application of the probe according to the invention can be most easily envisaged by dissolution in the agar solution before it is poured into the dish or gelifies itself. As an alternative, substrates are incubated with colonies by immersion of a filter before they are introduced into colonies. The principal benefit which the probe according to the invention contributes to such an analysis of colonies is the on-site precipitation of the fluorophore; dilution of the fluorescent signal is therefore very reduced, which makes long incubation periods possible and therefore, greater sensitivity for analysis. The very large Stokes shift of dichloro-HPQ (approximately 140 nm), or of any analog of HPQ, should not be misestimated; it also contributes to superior sensitivity, and the emitted fluorescence is easily distinguishable from the native fluorescence which could come from the biological sample.

Probes according to the invention can also be used for macroscopic fluorescence imaging, namely, for the entire organism. In this case, the probe will penetrate the cell wall in order to reach the activity of interest.

Examples, in relation to the annexed figures, make it possible to illustrate the invention, but not in a limitative way.

FIG. 1 is a diagram showing the degradation mechanism, using formula (I) compounds, calling on the pair of spacers according to the invention.

FIG. 2 is an evolution curve of the solid-state fluorescence for probes 13 and 27 of examples 1 and 3 and for probe 28 of the prior art at 37° C. (concentration: 10 μM).

EXAMPLES

General Information

Figure 1:
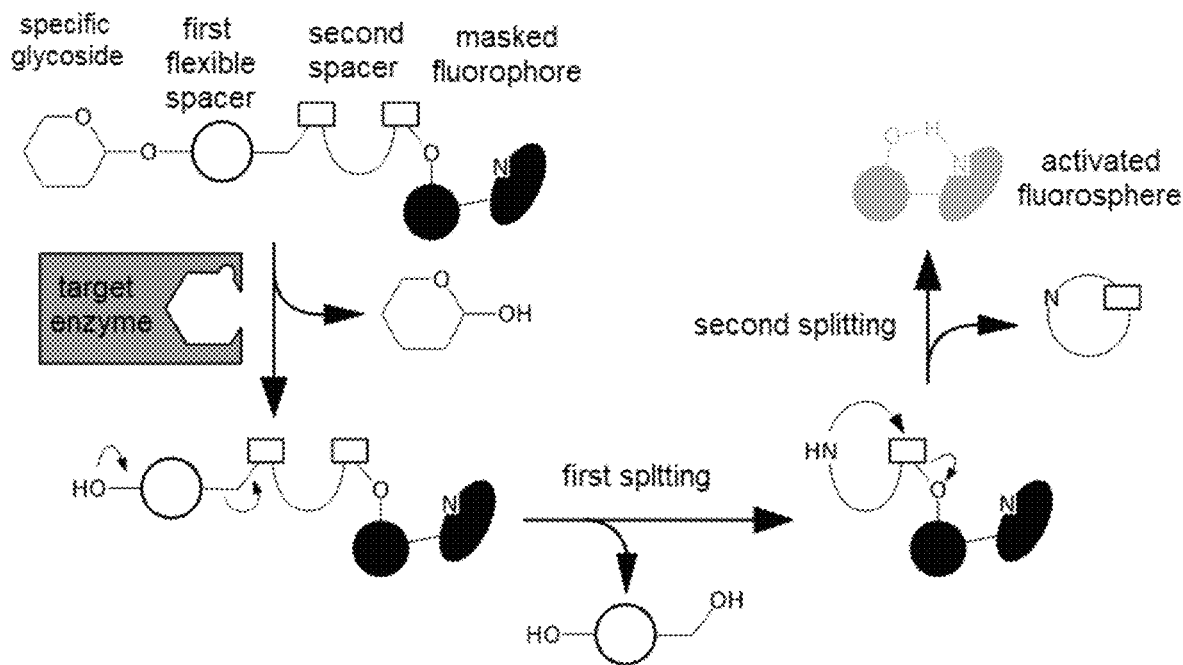

Column chromatography was conducted on 60-mesh silica gel (40-63 pm). The RMN spectra for 1H and 13C were recorded at 300 MHz and at 75 or 125 MHz, respectively, in deuterated chloroform, deuterated DMSO or deuterated methanol. Chemical displacements (5) are indicated in ppm and noted in reference to tetramethylsilane or according to residual solvent signals; the abbreviations s=singlet, d=doublet, t=triplet, m=multiplet, b=large are used. RMN (J) coupling constants are indicated in Hertz. Fluorescent analyses were conducted in 96-well black polypropelyne plates (Corning Costar, Corning, Inc.), and registered on a microplate fluorimeter (EnSpire plate reader by Perkin Elmer). Except when specified chemical products were purchased with analytic reactive quality and used without other purification.

Commercial dry DCM was dried and purified by passing it through an activated aluminum column under argon (GT S100 Solvent Station System). TEA was distilled using calcium hydride and stored in KOH pellets. The other reagents noted as dry were dried on molecular sieves. If not otherwise noted, all reactions were conducted under atmospheric air with solvents and commercial reagents, without additional drying or purification. Millipore water obtained using an Elga Purelab purification system was used in all experiments.

The following abbreviations are used:
DIPEA=diisopropylehtylamine
TEA=triethylamine
py=pyridine
DCM=dichloromethane
Yld.=yield
DMSO=dimethyl sulfoxide
TFA=trifluoroacetic acid
rt=room temperature.

Example 1

Compound 13 is prepared as described in Diagram 1 below.

Diagram 1: Chemical Synthesis of Compound 13

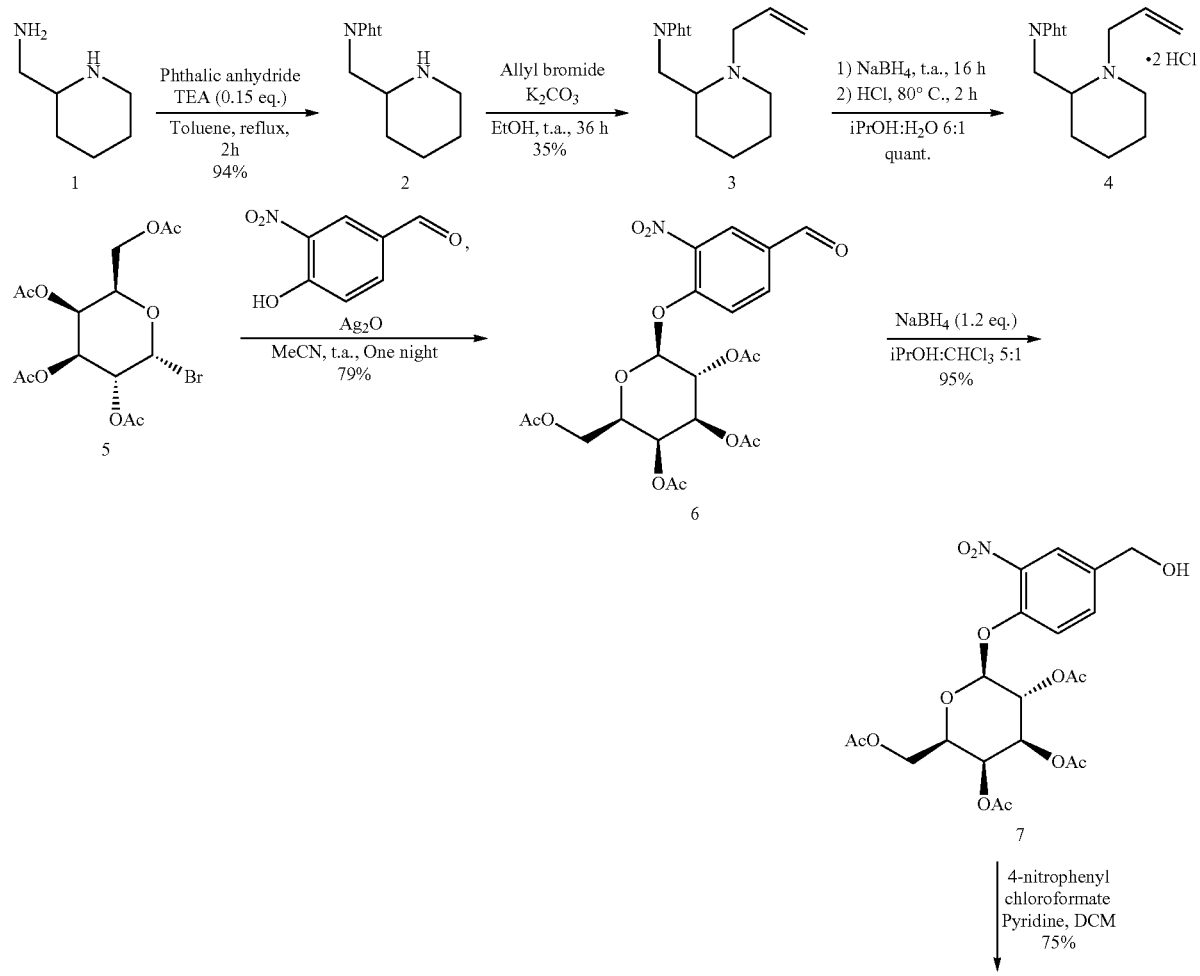

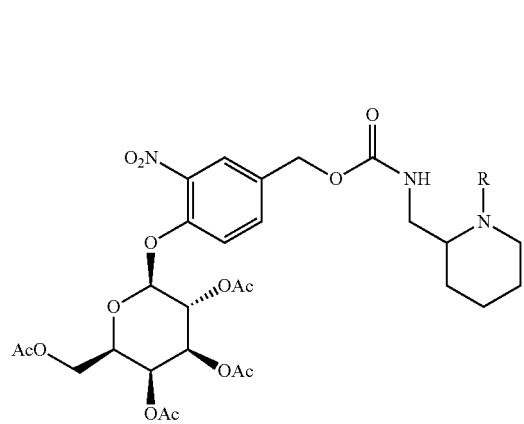
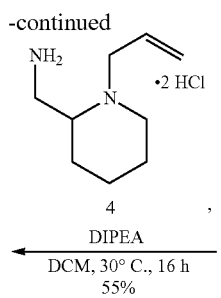
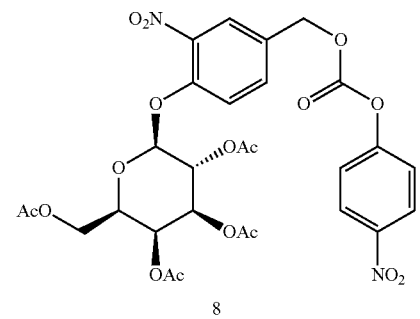
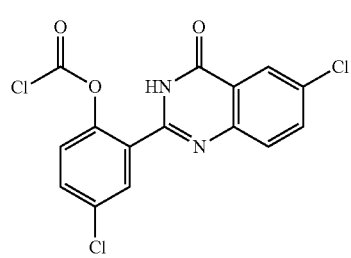
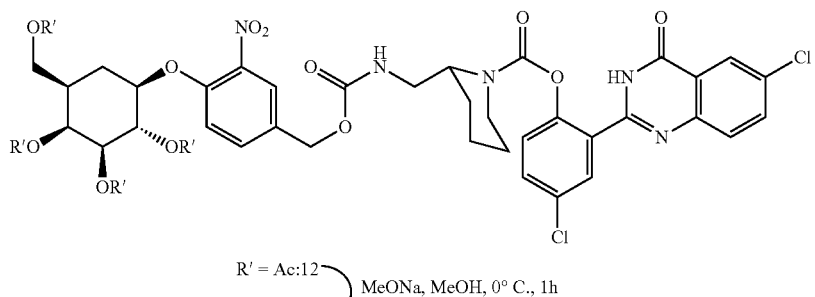

Preparation of Compound 2

To a solution of 2-aminoethylpiperidine 1 (3.0 g, 26.3 mmol, 1.0 eq.) in 100 mL of toluene was added, little by little, phthalic anhydride (3.89 g, 26.3 mmol, 1.0 eq.) and, drop by drop, triethylamine (550 µL, 3.95 mmol, 0.15 eq.). The mixture was then heated under reflux for 2 h using a Dean-Stark device. Then, the mixture was filtered and the solvent was evaporated under reduced pressure. Compound 2 (6.605 g, 24.7 mmol, yld: 94%) was obtained in the form of a light yellow solid and used without purification.

1H-NMR (300 MHz, CDCl3): δ (ppm)=7.89-7.82 (m, 2H), 7.75-7.68 (m, 2H), 3.68 (d, J=4 Hz, 2H), 3.13-3.05 (m, 1H), 2.98-2.88 (m, 1H), 2.64-2.54 (m, 1H), 1.87-1.78 (m, 1H), 1.76-1.68 (m, 1H), 1.63-1.54 (m, 1H), 1.45-1.34 (m, 2H), 1.30-1.15 (m, 1H).

13C-NMR (75 MHz, CDCl3): δ (ppm)=168.4, 133.7, 131.9, 123.0, 55.5, 46.4, 43.4, 30.6, 26.1, 24.1.

HRMS: ESI: [M+H]+ m/z found 245.1290, calc. 245.1290

Preparation of Compound 3

To a solution of compound 2 (6.605 g, 24.7 mmol, 1.0 eq.) in 80 mL of ethanol, cooled in an ice bath, potassium carbonate (4.36 g, 31.6 mmol, 1.3 eq.), tetra-n-butylammonium iodide (912 mg, 2.47 mmol, 0.10 eq.) and allyl bromide (2.73 mL, 31.6 mmol, 1.3 eq.) were added. The ice bath was removed and the mixture was stirred for 36 h. At the end of the reaction, the mixture was filtered with Celite and evaporated under reduced pressure. The residual oil was dissolved in EtOAc and an aqueous solution saturated in NH4Cl was added. The two phases were separated and the organic phase was washed two times with an aqueous solution saturated in NH4Cl. The combined aqueous phases were extracted 3 times with EtOAc. The combined organic phases were dried with Na2SO4, filtered and concentrated under reduced pressure. The raw product was purified by column chromatography on silica gel (pure DCM, then DCM:MeOH:Et3N/99:0.5:0.5/v:v:v) in order to obtain compound 3 in the form of a yellow oil that crystallizes (2.24 g, 7.89 mmol, yield: 35%).

1H-NMR (300 MHz, CDCl3): δ (ppm)=7.84-7.78 (m, 2H), 7.72-7.65 (m, 2H), 5.95-5.81 (m, 1H), 5.22-5.08 (m, 2H), 3.93 (dd, 1H, J=13 Hz, J=5 Hz), 3.73 (dd, 1H, J=13 Hz, J=8 Hz), 3.42 (dd, 1H, J=14 Hz, J=6 Hz), 3.21 (dd, 1H, J=14 Hz, J=6 Hz), 2.88-2.76 (m, 2H), 2.37-2.28 (m, 2H), 1.74-1.47 (m, 4H), 1.40-1.25 (m, 2H).

13C-NMR (75 MHz, CDCl3): δ (ppm)=168.3, 135.5, 133.8, 132.0, 123.0, 117.2, 57.6, 57.3, 50.3, 38.4, 28.1, 24.7, 22.0.

HRMS: ESI: [M+H]+ m/z found 285.1595, calc. 285.1603

Preparation of Compound 4

To a solution of 3 (1.312 g, 4.6 mmol, 1.0 eq.) in iPrOH:H2O/6:1/v:v (50 mL) cooled in ice was added, little by little, sodium borohydride (874 mg, 23 mmol, 5.0 eq.). After having been stirred at room temperature for one night, the pH was acidified to pH=1, using an aqueous solution of HCl at 37%. The mixture was filtered and then heated to 80° C. for 2 hours. iPrOH was evaporated under reduced pressure and the resulting aqueous solution was washed 5 times with diethyl ether and then lyophilized Compound 4 was obtained in the form of a white powder (1.045 g, 4.6 mmol, quantitative yld).

RMN of the basic product (1-allyl-2-(aminomethyl) piperidine): ° H-NMR (300 MHz, CDCl3): δ (ppm)=5.99-5.86 (m, 1H), 5.24-5.13 (m, 2H), 3.41 (ddt, 1H, J=14 Hz, J=5.7 Hz, J=1.5 Hz), 3.04-2.90 (m, 3H), 2.74 (dd, 1H, J=13 Hz, J=3.3 Hz), 2.21 (tt, 2H, J=9.6 Hz, =3.3 Hz), 1.80-1.71 (m, 1H), 1.68-1.43 (m, 2H), 1.39-1.25 (m, 3H).

13C-NMR (75 MHz, CDCl3): δ (ppm)=134.93, 116.87, 61.47, 56.23, 51.93, 42.97, 28.28, 24.95, 23.66.

HRMS: ESI: [M+H]+ m/z found 155.1543, calc. 155.1548

Preparation of Compound 6

Acetobromogalactose 5 (700 mg, 1.70 mmol, 1.0 eq.), of 4-hydroxy-3-nitrobenzaldehyde (313 mg, 1.87 mmol, 1.1 eq.) and Ag2O (1.300 g, 5.61 mmol, 3.3 eq.) were dissolved in acetonitrile and stirred for one night at room temperature. The reactional mixture was then filtered with Celite and concentrated under reduced pressure. The resulting oil was purified by column chromatography on silica gel (petroleum ether:ethyl acetate/4:6/v:v) in order to obtain compound 6 in the form of a light yellow solid (669 mg, 1.34 mmol, yld: 79%).

1H-MR (300 MHz, DMSO-d6): δ (ppm)=9.98 (s, 1H), 8.45 (d, J=2 Hz, 1H), 8.26 (dd, J=9 Hz, J=2 Hz, 1H), 7.60 (d, J=9 Hz, 1H), 5.80 (d, J=8 Hz, 1H), 5.40 (bs, 1H), 5.30-5.27 (m, 2H), 4.55 (td, J=6 Hz, J=1 Hz, 1H), 4.15 (d, J=6 Hz, 2H), 2.16 (s, 3H), 2.05 (s, 3H), 2.04 (s, 3H), 1.96 (s, 3H).

13C-NMR (75 MHz, CDCl3): δ (ppm)=188.55, 170.24, 170.07, 169.16, 153.45, 141.25, 133.96, 131.48, 126.84, 118.80, 100.09, 71.82, 70.35, 67.59, 66.58, 61.36, 20.66, 20.61, 20.59, 20.55.

HRMS: ESI: [M+Na]+ m/z found 520.1052, calc. 520.1067

Preparation of Compound 7

To a solution of compound 6 (636 mg, 1.28 mmol, 1.0 eq.) in CHCl3:iPrOH 5:1 v:v (12 mL) in an ice bath, was added sodium borohydride (53 mg, 1.41 mmol, 1.1 eq.). The reaction was stirred for 1 hour and halted by the addition of an aqueous solution saturated in NH4Cl.

After 5 minutes of stirring, the phases were separated and the aqueous phase was extracted 2 times with dichloromethane. The combined organic phases were dried with Na2SO4, filtered and evaporated under reduced pressure to give compound 7 in the form of a white powder.

(605 mg, 1.22 mmol, yld: 95%) which was used in the next step without purification.

1H-NMR (300 MHz, DMSO-d6): δ (ppm)=7.80 (d=2 Hz, 1H), 7.63 (dd, J=9 Hz, J=2 Hz, 1H), 7.37 (d, J=9 Hz, 1H), 5.56 (d, J=7 Hz, 1H), 5.43 (t, J=6 Hz, 1H), 5.37 (d, J=3 Hz, 1H), 5.31-5.19 (m, 2H), 4.53-4.45 (m, 3H), 4.19-4.08 (m, 2H), 2.16 (s, 3H), 2.04 (s, 6H), 1.95 (s, 3H).

13C-NMR (125 MHz, DMSO-d6): δ (ppm)=170.54, 170.46, 170.13, 169.47, 147.70, 140.84, 138.90, 132.41, 122.80, 118.30, 99.34, 71.35, 70.54, 68.34, 67.72, 61.94, 61.87, 21.10, 20.98, 20.92.

HRMS: ESI: [M+Na]+ m/z found 522.1209, calc. 522.1224

Preparation of Compound 8

To a solution of compound 7 (120 mg, 0.240 mmol, 1.0 eq.) in dry DCM (5 mL), cooled in ice was added, successively, 4-nitrophenyl chloroformate (107 mg, 0.53 mmol, 2.2 eq.) and pyridine (48 μL, 0.60 mmol, 2.5 eq.) drop by drop. The reaction mixture was stirred at 0° C. for 30 min and at room temperature for 2 h. At the end of the reaction, the reaction was stopped using an HCl 1 M aqueous solution and the phases were separated. The organic phase was washed with a solution of HCl 1 M, and the combined aqueous phases were extracted with DCM. The organic phases were dried with Na2SO4, filtered and evaporated under reduced pressure. The raw product was purified by column chromatography on silica gel (petroleum ether gradient: ethyl acetate/85:15 to 50:50/v:v) in order to obtain compound 7 in the form of a white solid (111 mg, 0.18 mmol, yld: 75%).

1H-NMR (300 MHz, CDCl3): δ (ppm)=8.32 (d, J=9 Hz, 2H), 7.94 (d, J=2 Hz, 1H), 7.64 (dd, J=9 Hz, J=2 Hz, 1H), 7.44-7.39 (m, 3H), 5.59 (dd, J=10 Hz, J=8 Hz, 1H), 5.52 (d, J=3 Hz, 1H), 5.33 (s, 2H), 5.17-5.14 (m, H), 4.30 (dd, J=11 Hz, J=7 Hz, 1H), 4.23-4.14 (m, 2H), 2.23 (s, 3H), 2.17 (s, 3H), 2.11 (s, 3H), 2.06 (s, 3H).

13C-NMR (125 MHz, CDCl3): δ=171.0, 137.8, 135.1, 129.4, 128.9, 128.9, 128.8, 128.4, 127.3, 127.2, 80.1, 62.8, 54.2, 53.0, 49.7, 43.9, 41.0, 40.1, 28.5 ppm.

MS: ESI: [M+Na]+ m/z found 687.1263, calc. 687.1286

Preparation of Compound 9

To a suspension of compound 4 (44 mg, 0.20 mmol, 1.3 eq.) in DCM (3 mL), was added compound 8 (100 mg, 0.150 mmol, 1.0 eq.). The reactional mixture was cooled in an ice bath and DIPEA (81 qL, 0.47 mmol, 3.1 eq.) was added. After 5 minutes, the ice bath was removed and the reactional mixture was heated to 30° C. for one night. The mixture was then washed with aqueous solutions saturated with Na2CO3 et NaHCO3, dried with Na2SO4, filtered and evaporated under reduced pressure. The raw product was purified by column chromatography on silica gel in order to obtain compound 9 in the form of a white solid (56 mg, 0.083 mmol, yld: 55%).

NMR: 1H-NMR (300 MHz, CDCl3): δ(ppm) J=7.82 (d, J=2 Hz, 1H), 7.53 (dd, J=9 Hz, J=2 Hz, 1H), 7.35 (d, J=9 Hz, 1H), 5.93-5.75 (m, 1H), 5.56 (dd, =10 Hz, J=8 Hz, 1H), 5.48 (d, =J/−3 Hz, 1H), 5.32 (bs, 1H), 5.22-5.06 (m, 6H), 4.29-4.14 (m, 2H), 4.11-4.06 (m, 1H), 3.43-3.22 (m, 3H), 2.99-2.8 (m, 2H), 2.43-2.36 (m, 1H), 2.21 (s, 3H), 2.14 (s, 3H), 2.09 (s, 3H), 2.03 (s, 3H), 1.76-1.25 (m, 6H).

13C-NMR (125 MHz, CDCl3): δ (ppm)=170.31, 170.19, 170.13, 169.40, 156.26, 148.92, 141.30, 134.68, 133.19, 133.14, 124.59, 119.83, 117.75, 100.82, 71.47, 70.57, 67.85, 66.75, 64.74, 61.37, 58.30, 56.36, 51.99, 42.51, 28.97, 25.00, 23.73, 20.70, 20.67, 20.59.

HRMS: ESI: [M+H]+ m/z found 680.2683, calc. 680.2667

Preparation of Compound 10

A solution of compound 9 (20 mg, 0.029 mmol, 1.0 eq.) and of 1,3-dimethylbarbituric acid (37 mg, 0.24 mmol, 8.0 eq.) in dry DCM (3 mL) was degassed with an argon flow. Then, palladium (0) tetrakis (triphenylphosphine) (0.6 mg, 0.0005 mmol, 2 mol %) was added. At the end of the reaction, the reactional mixture was dry evaporated and purified by column chromatography on silica gel in order to obtain compound 10 in the form of a white solid (13 mg, 0.020 mmol, yld: 70%).

1H-NMR (300 MHz, CDCl3): δ (ppm)=7.82 (d, J=2 Hz, 1H), 7.52 (dd, J=9 Hz, J=2 Hz, 1H), 7.35 (d, J=9 Hz, 1H), 5.56 (dd, J=10 Hz, J=8 Hz, 1H), 5.48 (d, J=3 Hz, 1H), 5.32-5.26 (m, 1H), 5.14-5.06 (m, 4H), 4.30-4.15 (m, 2H), 4.11-4.06 (m, 1H), 3.29-3.20 (m, 1H), 3.11-3.00 (m, 2H), 2.72-2.58 (m, 2H), 2.20 (s, 3H), 2.14 (s, 3H), 2.09 (s, 3H), 2.03 (s, 3H), 1.87-1.77 (m, 1H), 1.68-1.59 (m, 2H), 1.42-1.34 (m, 2H), 1.31-1.26 (m, 1H).

13C-NMR (125 MHz, CDCl3): δ (ppm)=170.32, 170.19, 170.14, 169.40, 156.15, 148.92, 141.30, 133.14, 133.10, 124.59, 119.84, 100.82, 71.48, 70.57, 67.85, 66.73, 64.73, 61.36, 56.03, 46.88, 46.68, 30.26, 26.47, 24.26, 20.70, 20.67, 20.59.

HRMS: ESI: [M+H]+ m/z found 640.2337, calc. 640.2354

Preparation of Compound 12

To suspension of compound 10 (13 mg, 0.020 mmol, 1.0 eq.) in dry DCM (2 mL) under an argon atmosphere and cooled in ice, was added, drop by drop, a solution of compound 11 (8 mg, 0.021 mmol, 1.05 eq.) and of DIPEA (10 qL, 0.060 mmol, 3.0 eq.). After the addition, the reactional mixture was mixed at 0° C. for 30 min, then at room temperature for one night. The reactional mixture was then washed with an aqueous solution saturated with NaHCO3, and the organic phase was dried with Na2SO4, filtered and evaporated under reduced pressure. The raw product was purified by column chromatography on silica gel in order to obtain compound 12 in the form of a white powder (10 mg, 0.010 mmol, yld: 52%).

1H-NMR (300 MHz, CDCl3): δ (ppm)=10.41-10.29 (m, 1H), 8.24 (bs, 1H), 8.16-8.05 (m, 1H), 7.85-7.63 (m, 2.5H), 7.57-7.46 (m, 2H), 7.45-7.37 (m, 0.5H), 7.25-7.08 (m, 2H), 6.23-6.10 (m, 0.5H), 5.83-5.75 (m, 0.5H), 5.57 (dd, J=10 Hz, J=8 Hz, 1H), 5.49 (d, J=3 Hz, 1H), 5.17-4.96 (m, 2H), 4.94-4.69 (m, 1H), 4.58 (bs, 1H), 4.33-3.99 (m, 4H), 3.79-3.63 (m, 1H), 3.39-3.01 (m, 2H), 2.21 (s, 3H), 2.16 (s, 3H), 2.09 (s, 3H), 2.04 (s, 3H), 1.82-1.24 (m, 6H).

13 C-NMR (125 MHz, CDCl3): δ (ppm)=170.36, 170.20, 170.14, 169.39, 161.09, 156.42, 152.66, 149.05, 147.37, 140.98, 139.32, 135.29, 133.30, 132.64, 132.37, 130.70, 129.72, 127.87, 125.88, 125.39, 125.04, 124.39, 124.03, 122.30, 119.77, 114.09, 100.76, 71.43, 70.62, 67.84, 66.73, 64.44, 61.31, 40.84, 29.72, 29.40, 25.38, 22.72, 20.69, 20.60, 18.89.

HRMS: ESI: [M+H]+ m/z found 972.2077, calc. 972.2109

Preparation of Compound 13

To a solution of compound 12 (10 mg, 0.010 mmol, 1.0 eq.) in dry methanol, in an ice bath, was added sodium methoxyde (1.1 mg, 0.020 mmol, 2.0 eq.). The reactional mixture was stirred for 1 h at 0° C. Then the reaction was stopped with Dowex@50X8-100 resin, then filtered and concentrated under reduced pressure. Product 13 was obtained in the form of a white resin (8 mg, 0.010 mmol, quantitative ryld). A high purity was obtained using HPLC in reverse phase (isocratic, water:acetonitrile, 1:1 v:v with 0.1% TFA) to give compound 13 in the form of a white powder.

1H-NMR (300 MHz, CD3OD): δ (ppm)=8.07 (m, 1H), 7.73-7.69 (m, 2H), 7.67-7.60 (m, 2H), 7.50-7.31 (m, 2H), 7.31-7.23 (m, 1H), 7.13-7.05 (m, 1H), 5.02-4.93 (m, 1H), 4.93-4.82 (m, 2H), 4.51-4.40 (m, 1H), 4.13-4.03 (m, 1H), 3.83-3.78 (m, 1H), 3.77-3.71 (m, 1H), 3.68-3.58 (m, 3H), 3.53-3.44 (m, 2H), 3.12-3.01 (m, 1H), 2.94-2.83 (m, 1H), 1.59-1.25 (m, 6H).

13C-NMR (125 MHz, CD3OD): δ (ppm)=163.06, 158.56, 154.58, 152.42, 151.11, 149.16, 148.62, 141.78, 136.22, 134.26, 134.07, 132.97, 132.68, 132.09, 131.01, 130.43, 129.97, 126.45, 126.12, 125.42, 125.22, 123.48, 118.91, 103.10, 96.37, 77.36, 74.86, 71.96, 70.10, 65.76, 62.32, 53.19, 52.68, 41.16, 27.00, 26.27, 19.86.

HRMS: ESI: m/z [M+H]+ found: 804.1671 calc. 804.1687

Example 2

Compound 21 is prepared as described in Diagram 2 below.

Diagram 2: Chemical Synthesis of Compound 21

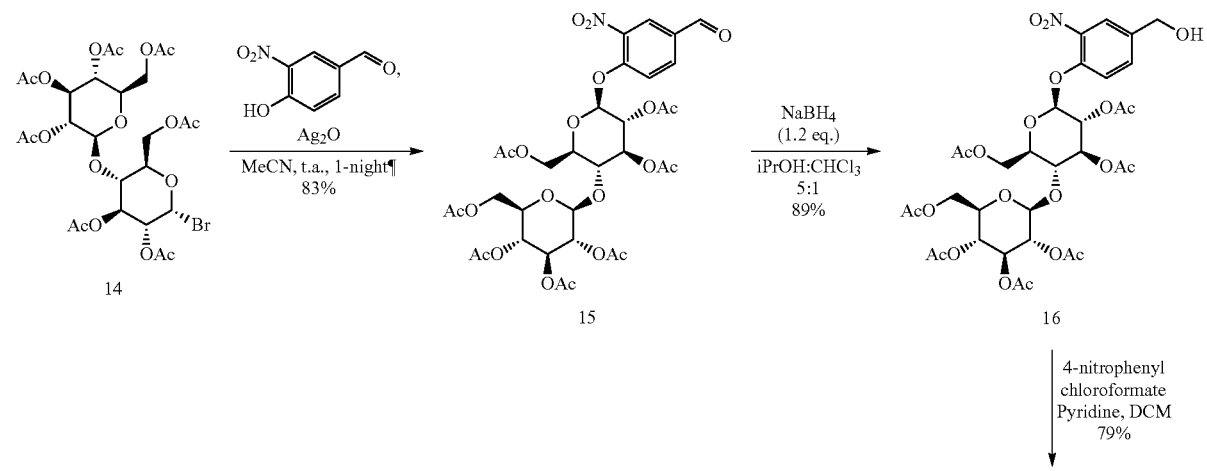

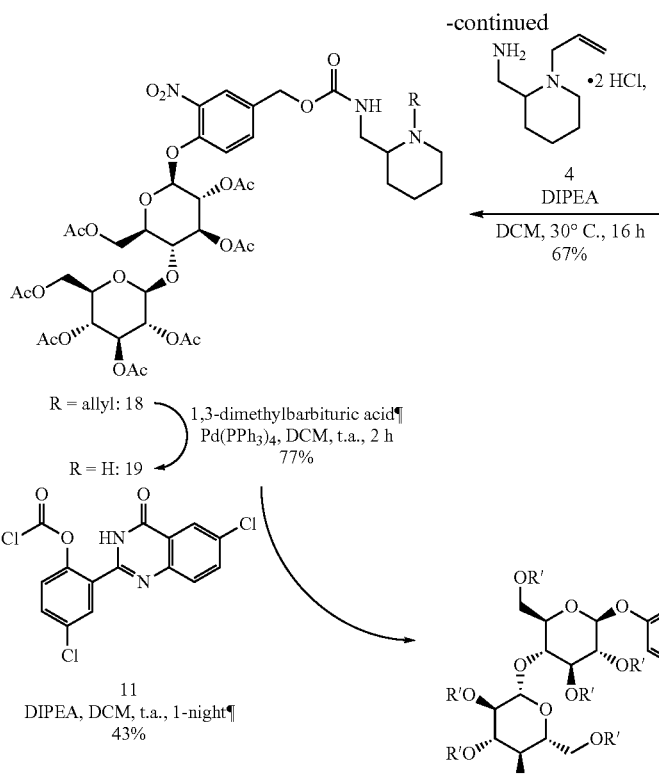
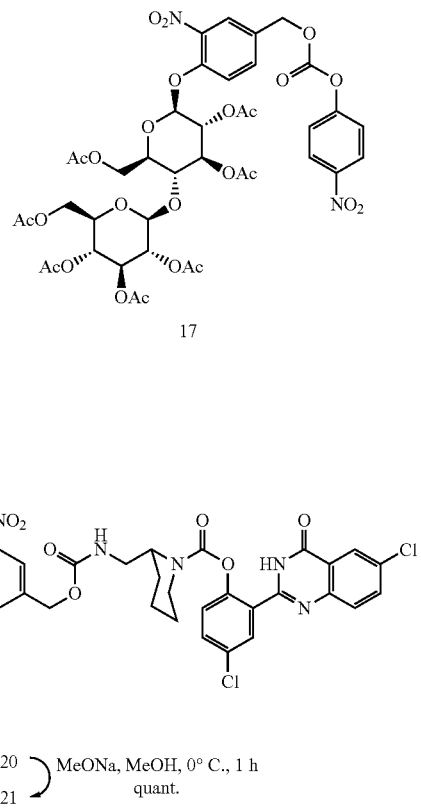

Preparation of Compound 15

A method analogous to that used for the preparation of compound 6 was used using acetobromo-D-cellobiose 14 (2 g, 2.86 mmol, 1.0 eq.), of 4-hydroxy-3-nitrobenzaldehyde (478 mg, 2.86 mmol, 1.0 eq.) and Ag2O (729 mg, 3.15 mmol, 1.1 eq.)) in order to obtain compound 15 in the form of a light yellow solid (1.864 g, 2.37 mmol, yld: 83%).

1H-NMR (300 MHz, CDCl3): δ (ppm)=9.98 (s, 1H), 8.30 (d, J=2 Hz, 1H), 8.07 (dd, J=9 Hz, J=2 Hz, 1H), 7.43 (d, J=9 Hz, 1H), 5.35-5.05 (m, 5H), 4.95 (t, J=8 Hz, 1H), 4.64-4.57 (m, 2H), 4.38 (dd, J=13 Hz, J=4 Hz, 1H), 4.16-3.98 (m, 3H), 3.94-3.87 (m, 1H), 3.74-3.67 (m, 1H), 2.12 (s, 3H), 2.11 (s, 3H), 2.08 (s, 3H), 2.04 (s, 3H), 2.03 (s, 3H), 2.02 (s, 3H), 2.00 (s, 3H).

13C-NMR (125 MHz, CDCl3): δ (ppm)=189.23, 170.88, 170.54, 170.46, 170.11, 169.71, 169.68, 169.47, 153.68, 141.40, 134.58, 131.65, 127.10, 118.64, 101.22, 98.98, 76.24, 73.60, 73.19, 72.39, 71.93, 70.97, 68.11, 61.91, 21.02, 20.88, 20.86.

HRMS: ESI: [M+Na]+ m/z found 808.1874, calc. 808.1912

Preparation of Compound 16

A method analogous to that used for the preparation of compound 7 was used using compound 15 (650 g, 0.83 mmol, 1.0 eq.), and NaBH4 (34 mg, 0.91 mmol, 1.1 eq.) in order to obtain compound 16 in the form of a white powder pour (580 mg, 0.74 mmol, yld: 89%), which was used in the next reaction without purification.

1H-NMR (300 MHz, CDCl3): δ (ppm)=7.82 (d, J=2 Hz, 1H), 7.54 (dd, J=9 Hz, J=2 Hz, 1H), 7.32 (d, J=9 Hz, 1H), 5.31-5.06 (m, 5H), 4.97 (t, J=8 Hz, 1H), 4.74 (d, J=6 Hz, 1H), 4.64-4.57 (m, 2H), 4.40 (dd, J=13 Hz, =4 Hz, 1H), 4.15-4.07 (m, 2H), 4.01-3.95 (m, 1H), 3.84-3.78 (m, 1H), 3.74-3.68 (m, 1H), 2.14 (s, 3H), 2.12 (s, 3H), 2.09 (s, 3H), 2.08 (s, 3H), 2.06 (s, 3H), 2.04 (s, 3H), 2.01 (s, 3H), 1.87 (t, J=6 Hz, 1H).

13C-NMR (125 MHz, CDCl3): δ (ppm)=170.48, 170.20, 170.12, 169.79, 169.54, 169.32, 169.11, 148.15, 141.10, 137.49, 131.78, 123.00, 119.23, 100.71, 99.61, 76.01, 73.04, 72.86, 72.23, 71.95, 71.60, 70.85, 67.83, 63.04, 61.63, 61.57, 20.60, 20.54, 20.41.

HRMS: ESI: [M+Na]+ m/z found 810.2022, calc. 810.2069

Preparation of Compound 17

A method analogous to that used for the preparation of compound 8 was used using compound 16 (400 mg, 0.51 mmol, 1.0 eq.), 4-nitrophenyl chlorformate (225 mg, 1.07 mmol, 2.2 eq.) and pyridine (102 μL, 1.27 mmol, 2.5 eq.) in order to obtain compound 17 in the form of a white powder (380 mg, 0.40 mmol, yld: 79%).

1H-NMR (300 MHz, CDCl3): δ (ppm)=8.32 (d, J=9 Hz, 2H), 7.92 (d, J=2 Hz, 1H), 7.63 (dd, J=9 Hz, J=2 Hz, 1H), 7.41 (d, J=9 Hz, 2H), 7.35 (d, J=9 Hz, 2H), 5.32-5.07 (m, 5H), 4.97 (t, J=8 Hz, 1H), 4.67-4.58 (m, 2H), 4.64-4.57 (m, 2H), 4.40 (dd, J=13 Hz, J=4 Hz, 1H), 4.15-4.06 (m, 2H), 4.03-3.97 (m, 1H), 3.87-3.81 (m, 1H), 3.74-3.68 (m, 1H), 2.14 (s, 3H), 2.12 (s, 3H), 2.09 (s, 3H), 2.08 (s, 3H), 2.06 (s, 3H), 2.04 (s, 3H), 2.01 (s, 3H).

13C-NMR (75 MHz, CDCl3): δ (ppm)=170.51, 170.07, 170.05, 169.68, 169.33, 169.28, 169.03, 155.27, 152.18, 149.47, 145.42, 140.92, 133.94, 130.03, 125.35, 125.29, 121.71, 119.05, 100.75, 99.22, 75.98, 73.09, 72.80, 72.09, 71.91, 71.54, 70.70, 68.81, 67.74, 61.56, 61.53, 0.60, 20.55, 20.42.

HRMS: ESI: [M+Na]+ m/z found 975.2103, calc. 975.2131

Preparation of Compound 18

A method analogous to that used for the preparation of compound 9 was used, using compound 17 (100 mg, 0.11 mmol, 1.0 eq.), 4 (30 mg, 0.20 mmol, 1.3 eq.) and DIPEA (40 μL, 0.23 mmol, 2.1 eq.) in order to obtain compound 18 in the form of a white solid (68 mg, 0.070 mmol, yld: 67%).

1H-NMR (300 MHz, CDCl3): δ (ppm)=7.82 (d, J=2 Hz, 1H), 7.53 (dd, J=9 Hz, J=2 Hz, 1H), 7.28 (d, J=9 Hz, 1H), 5.94-5.80 (m, 1H), 5.44-5.06 (m, 9H), 4.96 (t, J=8 Hz, 1H), 4.64-4.56 (m, 2H), 4.40 (dd, J=13 Hz, J=4 Hz, 1H), 4.15-4.06 (m, 2H), 4.01-3.95 (m, 1H), 3.84-3.78 (m, 1H), 3.73-3.67 (m, 1H), 3.44-3.24 (m, 3H), 3.05-2.91 (m, 2H), 2.42 (bs, 1H), 2.22 (t, =11 Hz, 1H), 2.13 (s, 3H), 2.12 (s, 3H), 2.08 (s, 6H), 2.05 (s, 3H), 2.03 (s, 3H), 2.01 (s, 3H), 1.77-1.26 (m, 6H).

13C-NMR (75 MHz, CDCl3): δ (ppm)=170.49, 170.18, 170.12, 169.72, 169.47, 169.29, 169.02, 156.20, 148.73, 141.14, 134.66, 133.19, 132.93, 124.56, 119.18, 117.69, 100.80, 99.37, 75.94, 73.01, 72.86, 72.18, 72.06, 71.59, 70.84, 67.74, 64.64, 61.51, 61.48, 58.28, 56.31, 51.93, 42.47, 28.93, 24.94, 23.67, 20.69, 20.64, 20.54, 20.52.

HRMS: ESI: [NI+H]+ m/z found 968.3545, calc. 968.3512

Preparation of Compound 19

A method analogous to that used for the preparation of compound 10 was used, using compound 18 (68 mg, 0.070 mmol, 1.0 eq.), 1, 3-dimethylbarbituric acid (86 mg, 0.56 mmol, 8.0 eq.) and palladium(0) tetrakis (triphenylphosphine) (1.6 mg, 0.0014 mmol, 2 mol %) in order to obtain compound 19 in the form of a white solid (49 mg, 0.053 mmol, yld: 77%).

1H-NMR (300 MHz, CDCl3): δ (ppm)=7.79 (d, J=2 Hz, 1H), 7.51 (dd, J=9 Hz, J=2 Hz, 1H), 7.27 (d, J=9 Hz, 1H), 5.49-5.42 (m, 1H), 5.29-5.04 (m, 7H), 4.95 (t, J=8 Hz, 1H), 4.63-4.55 (m, 2H), 4.39 (dd, J=13 Hz, J=4 Hz, 1H), 4.14-4.04 (m, 2H), 4.00-3.93 (m, 1H), 3.84-3.78 (m, 1H), 3.73-3.67 (m, 1H), 3.30-3.21 (m, 1H), 3.12-3.02 (m, 2H), 2.70-2.62 (m, 2H), 2.13 (s, 3H), 2.12 (s, 3H), 2.08 (s, 6H), 2.05 (s, 3H), 2.03 (s, 3H), 2.01 (s, 3H), 1.85-1.12 (m, 6H).

13C-NMR (75 MHz, CDCl3): δ (ppm)=170.50, 170.20, 170.12, 169.72, 169.48, 169.30, 169.02, 156.10, 148.74, 141.15, 133.18, 132.84, 124.56, 119.20, 100.82, 99.36, 75.93, 73.02, 72.87, 72.19, 72.08, 71.60, 70.85, 67.75, 64.68, 61.53, 61.47, 56.00, 46.83, 46.63, 30.22, 26.42, 24.22, 20.70, 20.66, 20.55, 20.53.

HRMS: ESI: [M+H]+ m/z found 928.3230, calc. 928.3199

Preparation of Compound 20

A method analogous to that used for the preparation of compound 12 was used using compound 19 (49 mg, 0.053 mmol, 1.0 eq.), 11 (21 mg, 0.054 mmol, 1.05 eq.) and DIPEA (28 μL, 0.16 mmol, 3.0 eq.) in order to obtain compound 20 in the form of a white powder. (29 mg, 0.023 mmol, yld: 43%).

1H-NMR (300 MHz, CDCl3): δ (ppm)=10.52 (bs, 1H), 8.21 (bs, 1H), 8.10-7.97 (m, 1H), 7.76-7.64 (m, 2.5H), 7.56 (m, 0.5H), 7.50-7.43 (m, 2H), 7.18-7.09 (m, 2H), 6.17-6.07 (m, 0.5H), 5.76 (bs, 0.5H), 5.30-5.04 (m, 5H), 4.95 (t, =8 Hz, 1H), 4.91-4.72 (m, 2H), 4.63-4.48 (m, 3H), 4.40 (dd, J=13 Hz, J=4 Hz, 1H), 4.19-4.04 (m, 3H), 4.00-3.93 (m, 1H), 3.83-3.57 (m, 3H), 3.37-3.18 (m, 1.5H), 3.11-2.98 (m, 0.5H), 2.12 (s, 3H), 2.11 (s, 3H), 2.08 (s, 3H), 2.06 (s, 6H), 2.03 (s, 3H), 2.01 (s, 3H), 1.81-1.44 (m, 6H).

13C-NMR (75 MHz, CDCl3): δ (ppm)=170.52, 170.21, 170.18, 169.74, 169.50, 169.31, 169.04, 161.13, 156.33, 154.23, 152.63, 149.11, 147.57, 147.34, 140.89, 135.28, 133.22, 132.80, 132.24, 130.59, 129.54, 127.82, 126.91, 125.85, 125.24, 124.84, 124.17, 122.22, 119.11, 100.85, 99.30, 75.97, 72.98, 72.90, 72.24, 72.20, 72.08, 71.61, 70.85, 67.76, 64.47, 61.53, 61.48, 51.46, 40.79, 26.03, 25.27, 20.70, 20.67, 20.54, 18.84.

HRMS: ESI: [M+H]+ m/z found 1260.2914, calc. 1260.2954

Preparation of Compound 21

A method analogous to that used for the preparation of compound 13 was used, using compound 20 (23 g, 0.018 mmol, 1.0 eq.), and sodium methoxyde (1.0 mg, 0.036 mmol, 2.0 eq.) in order to obtain compound 21 in the form of a white powder (17 mg, 0.017 mmol, yld: 97%).

1H-NMR (300 MHz, CDCl3): δ (ppm)=8.19 (bs, 1H), 7.85-7.81 (m, 2H), 7.79-7.72 (m, 2H), 7.62-7.43 (m, 2H), 7.40-7.33 (m, 1H), 7.27-7.17 (m, 2H), 5.14-5.04 (m, 1.5H), 4.99-4.94 (m, 1H), 4.62-4.52 (m, 0.5H), 4.47 (d, =8 Hz, 2H), 4.26-4.16 (m, 1H), 3.97-3.82 (m, 3H), 3.74-3.56 (m, 5H), 3.44-3.35 (m, 3.5H), 3.30-2.95 (m, 3H), 3.11-2.98 (m, 0.5H), 1.72-1.15 (m, 6H).

13C-NMR (75 MHz, CDCl3): δ (ppm)=161.65, 157.10, 153.33, 153.05, 150.98, 149.35, 148.93, 147.75, 147.23, 140.47, 134.82, 132.84, 132.67, 131.57, 130.77, 129.62, 129.05, 128.55, 125.05, 123.86, 122.08, 117.46, 103.16, 100.77, 78.53, 76.75, 76.50, 75.55, 74.94, 73.51, 73.00, 72.99, 69.98, 64.34, 61.05, 60.19, 51.29, 39.52, 25.73, 24.79, 18.46.

HRMS: ESI: [M+H]+ m/z found: 966.2201, calc. 966.2215

Example 3

Compound 21 is prepared as described in Diagram 3 below.

Diagram 3: Chemical Synthesis of Compound 27

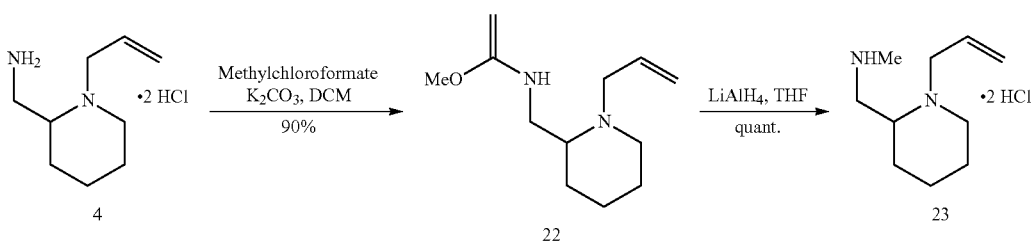

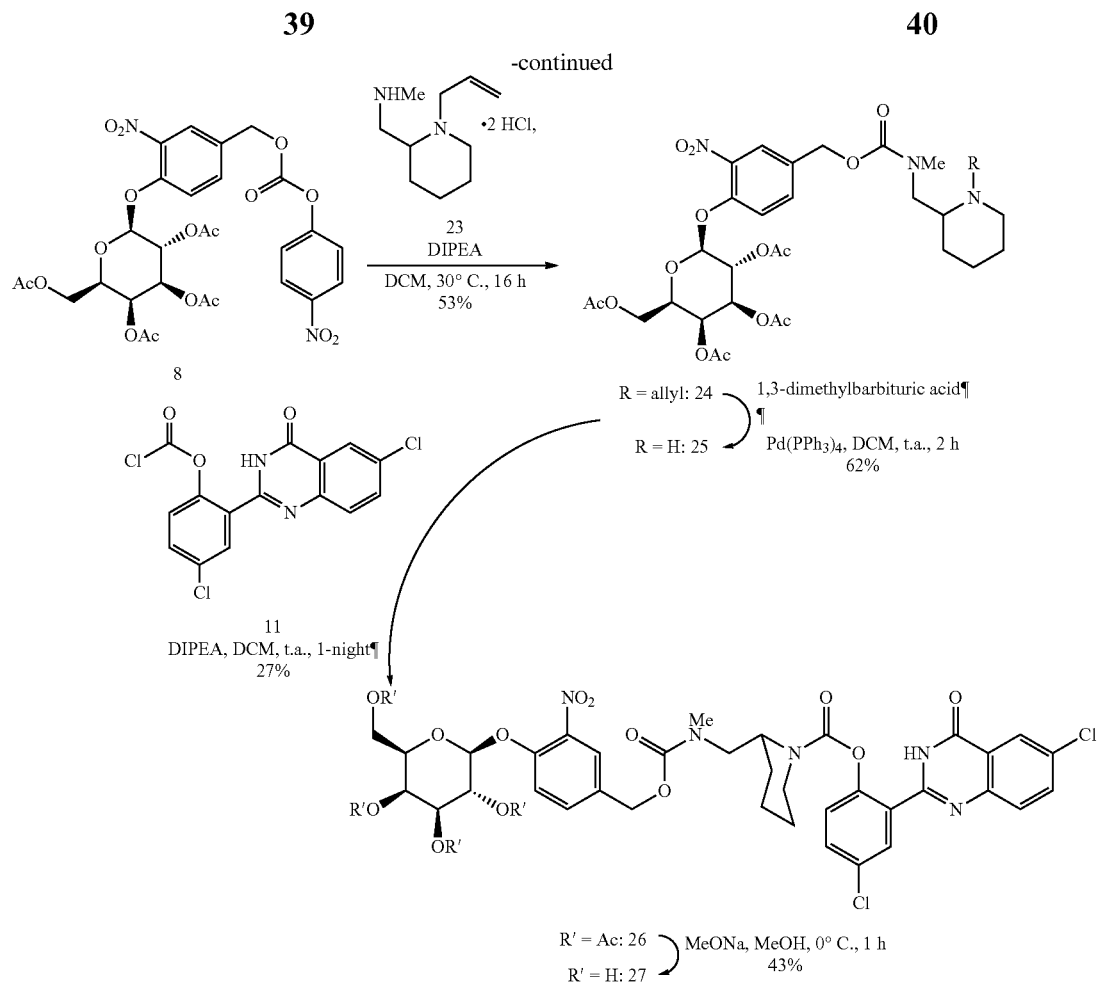

Preparation of Compound 22

To a solution of 3 (335 mg, 1.48 mmol, 1.0 eq.) in 5 mL in dichloromethane were added potassium carbonate (636 mg, 4.6 mmol, 3.1 eq.) and, drop by drop, methyl chlorformate (115 μL, 1.48 mmol, 1.0 eq.). After stirring for 10 minutes at room temperature, the solvent was evaporated under reduced pressure. The raw product was purified by column chromatography on silica gel in order to obtain compound 22 in the form of a light, yellow oil (282 mg, 1.33 mmol, yld: 90%).

1H-NMR (300 MHz, CDCl3): δ (ppm)=5.96-5.82 (m, 1H), 5.24-5.16 (m, 3H), 3.69 (s, 3H), 3.41-3.30 (m, 3H), 3.01-2.91 (m, 2H), 2.40 (m, 1H), 2.23-2.17 (m, 1H), 1.75-1.70 (m, 1H), 1.60-1.56 (m, 2H), 1.54-1.40 (m, 2H), 1.37-1.24 (m, 1H).

13C-NMR (75 MHz, CDCl3): δ (ppm)=157.34, 134.50, 117.71, 58.62, 56.29, 51.90, 42.31, 28.85, 24.92, 23.58.

HRMS: ESI: [NI+H]+ m/z found 213.1601, calc. 213.1603

Preparation of Compound 23

To a solution of lithium tetrahydro aluminate (2.64 mmol, 2.0 eq.) in 5 mL of tetrahydrofuran, 22 (280 mg, 1.32 mmol, 1.0 eq.) was added, drop by drop, and the medium was stirred at 40° C. for one night. The solvent was evaporated and product 23 was used without purification.

H-NMR (300 MHz, CDCl3): δ (ppm)=5.97-5.82 (m, 1H), 5.24-5.08 (m, 2H), 3.43-3.33 (m, 1H), 2.98-2.84 (m, 2H), 2.71-2.53 (m, 3H), 2.46-2.30 (m, 3H), 2.23-2.12 (m, 2H), 1.83-1.23 (m, 8H).

13C-NMR (75 MHz, CDCl3): δ (ppm)=127.43, 124.84, 61.65, 58.05, 55.71, 52.99, 52.19, 50.49, 48.26, 45.28, 34.14, 27.96, 26.19, 21.68, 21.43, 20.96, 20.02.

Preparation of Compound 24

A method analogous to that used for the preparation of compound 9 was used using compound 8 (150 mg, 0.23 mmol, 1.0 eq.), 23 (100 mg, 0.42 mmol, 1.8 eq.) and DIPEA (300 qL, 1.72 mmol, 7.6 eq.) in order to obtain compound 24 in the form of a white solid (84 mg, 0.12 mmol, yld: 53%).

1H-NMR (500 MHz, CDCl3): δ (ppm)=7.75 (s, 1H), 7.48 (dd, J=9 Hz, J=2 Hz, 1H), 7.30 (d, =9 Hz, 1H), 5.90-5.72 (m, 1H), 5.50 (dd, J=10 Hz, J=8 Hz, 1H), 5.42 (d, J=3 Hz, 1H), 5.14 (d, J=6 Hz, 1H), 5.12-4.99 (m, 6H), 4.25-4.11 (m, 2H), 4.11-4.01 (m, 1H), 3.58-3.47 (m, 1H), 3.35-3.19 (m, 2H), 3.09-2.96 (m, 1H), 2.88 (d, J=3 Hz, 3H), 2.81-2.71 (m, 1H), 2.68-2.58 (m, 1H), 2.14 (s, 3H), 2.08 (s, 3H), 2.02 (s, 3H), 1.97 (s, 3H), 1.70-1.36 (m, 6H).

13C-NMR (125 MHz, CDCl3): δ (ppm)=170.29, 170.18, 170.11, 169.38, 156.04, 148.92, 141.16, 135.08, 133.27, 133.23, 124.60, 119.66, 117.51, 100.69, 71.41, 70.53, 67.81, 66.74, 65.25, 61.36, 57.46, 57.10, 51.26, 49.88, 35.68, 30.92, 29.67, 28.20, 24.90, 22.60, 20.64.

LRMS: ESI: [M+H]+ m/z found 694.2, calc. 694.2823.

Preparation of Compound 25

A method analogous to that used for the preparation of compound 10 was used using compound 24 (84 mg, 0.12 mmol, 1.0 eq.), 1,3-Dimethylbarbituric acid (95 mg, 0.61 mmol, 5.0 eq.) and palladium(0) tetrakis (triphenylphosphine (1 mg, 0.0012 mmol, 1 mol %) in order to obtain compound 25 in the form of a white solid (49 mg, 0.07 mmol, yld: 62%).

1H-NMR (500 MHz, CDCl3): δ (ppm)=7.78 (d, J=9 Hz, 1H), 7.49 (d, J=8 Hz, 1H), 7.30 (d, J=9 Hz, 1H), 5.51 (dd, J=10 Hz, J=8 Hz, 1H), 5.43 (d, J=3 Hz, 1H), 5.32-5.26 (m, 1H), 5.13-4.98 (m, 4H), 4.24-4.19 (m, 1H), 4.16-4.10 (m, 1H), 4.08-4.03 (m, 1H), 3.26-3.19 (m, 1H), 3.18-3.12 (m, 1H), 3.06-3.01 (m, 1H), 2.93 (d, J=7 Hz, 3H), 2.82-2.68 (m, 1H), 2.61-2.51 (m, 1H), 2.15 (s, 3H), 2.09 (s, 3H), 2.04 (s, 3H), 1.98 (s, 3H), 1.79-1.75 (m, 1H), 1.61-1.50 (m, 2H), 1.42-1.20 (m, 3H).

13C-NMR (125 MHz, CDCl3): δ (ppm)=170.34, 170.22, 170.16, 169.42, 156.23, 148.93, 141.26, 133.30, 133.20, 124.59, 119.74, 100.77, 71.47, 70.57, 67.86, 66.77, 65.28, 61.39, 55.55, 55.12, 46.80, 36.00, 30.56, 26.30, 24.35, 20.72, 20.70, 20.62.

HRMS: ESI: [M+H]+ m/z found 654.2484, calc. 654.2504

Preparation of Compound 26

A method analogous to that used for the preparation of compound 12 was used using compound 25 (25 mg, 0.04 mmol, 1.0 eq.), 11 (21 mg, 0.04 mmol, 1.0 eq.) and DIPEA (33 μL, 0.19 mmol, 5.0 eq.) in order to obtain compound 26 in the form of a white powder (10 mg, 0.01 mmol, yld: 27%).

1H-NMR (300 MHz, CDCl3): δ (ppm)=10.65-10.32 (m, 1H), 8.27-8.14 (m, 1H), 8.06-7.90 (m, 1H), 7.86-7.67 (m, 3H), 7.57-7.46 (m, 1H), 7.46-7.34 (m, 1H), 7.34-7.21 (m, 1H), 7.11-7.03 (m, 1H), 5.56-5.49 (m, 1H), 5.46 (br s, 1H), 5.13-4.98 (m, 2H), 4.98-4.67 (m, 1H), 4.55 (br s, 1H), 4.31-3.97 (m, 4H), 3.93-3.78 (m, 1H), 3.28-3.03 (m, 2H), 3.01-2.88 (m, 3H), 2.19 (s, 3H), 2.12 (s, 3H), 2.04 (s, 3H), 2.01 (s, 3H), 1.78-1.23 (m, 6H).

13C-NMR (75 MHz, CDCls): δ (ppm)=170.41, 170.30, 170.25, 169.52, 160.53, 156.49, 153.10, 149.15, 147.52, 141.32, 139.29, 135.29, 133.31, 132.92, 132.28, 130.79, 129.79, 127.87, 126.09, 125.49, 125.13, 124.45, 124.38, 122.55, 119.83, 114.28, 100.84, 71.54, 70.67, 67.94, 66.82, 65.99, 61.42, 40.78, 29.83, 29.46, 26.68, 25.40, 20.78, 20.70, 20.54, 19.04.

HRMS: ESI: [M+H]+ m/z found 986.2219, calc. 986.2260

Preparation of Compound 27

A method analogous to that used for the preparation of compound 13 was used, using compound 26 (10 g, 0.01 mmol, 1.0 eq.), and sodium methoxyde (2.0 mg, 0.04 mmol, 3.5 eq.) in order to obtain compound 27 in the form of a white powder (3.57 mg, 0.004 mmol, yld: 43%).

Resolution of the RMN spectra is too low to be useful.

HRMS: ESI: [M+H]+ m/z found: 818.1838, calc. 818.1838

Example 4

Probes 13, 21 and 27 according to the invention were evaluated by incubation with the target enzyme, β-galactosidase (EC 3.2.1.23; "b-gal"; commercial) in an in vitro medium in multi-well micro-plates designed for fluorescence readers. The probes were evaluated using the following criteria:

detection of the elevated fluorescence intensity generated by the presence of enzyme activity ("on"),
detection of the complete absence ("off") of fluorescence in samples that do not contain the target enzyme (no intrinsic fluorescence),
detection of the absence of any hydrolytic degradation of the probe over time, demonstrating the robustness of the probe at pH 7 in an aqueous medium (no false positive signal),
detection of the rapidity of response to the presence of enzyme activity making it possible to reach a maximum signal quickly,
detection of improved kinetics of the two-spacer probe,
detection of high photo-stability of the solid fluorophore generated under extended irradiation by the fluorescence reader.

These results were compared with those obtained with a probe from the prior art (compound I. 1 of application WO 2014/020285) comprising a cyclizing type spacer (28):

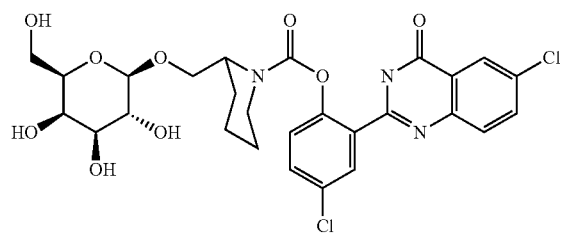

(28)

Protocol for the Detection of Fluorescence:

10 mM probe parent solutions in MeOH were diluted with PBS (Dulbecco's Phosphate Buffer Saline, Invitrogen Corp.) in order to obtain solutions with concentration ranges from 50 μM to 1 mM. Ten μL of each of these solutions was added to 80 μL of PBS in a 96-well black plate, and heated to 37° C. before the addition of the purified enzyme. Final probe concentrations were in the range of 5 μL to 100 μL. The plate was then incubated at 37° C. (or 25° C.) and fluorescence was measured over time by a fluorescence reader (EnSpire, Perkin Elmer; acquisition wavelengths: $\lambda_{ex}$=355 nm, $\lambda_{em}$=530 nm). The resulting curves are the mean of the duplicates.

Figure 2:
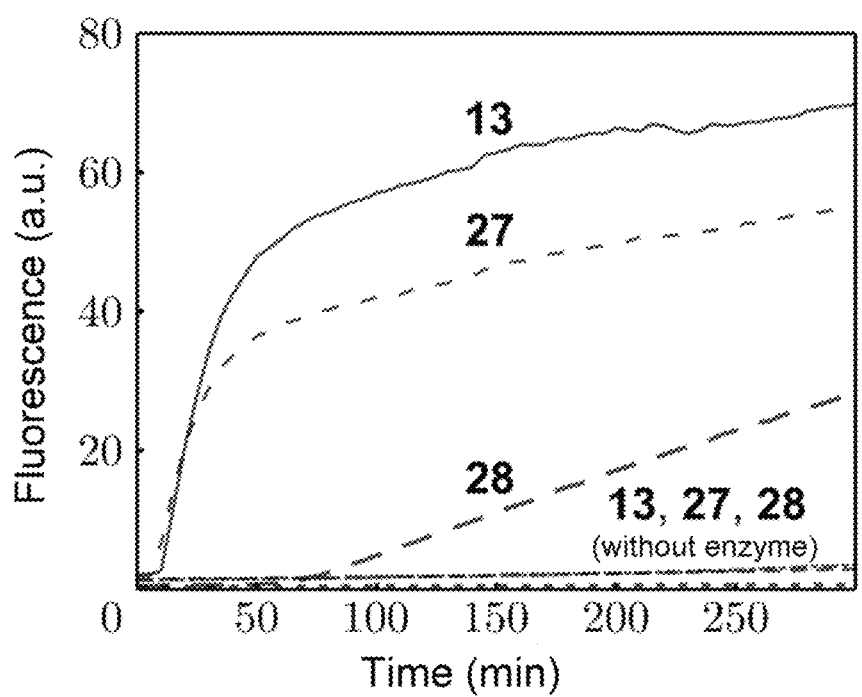
Figure 3:
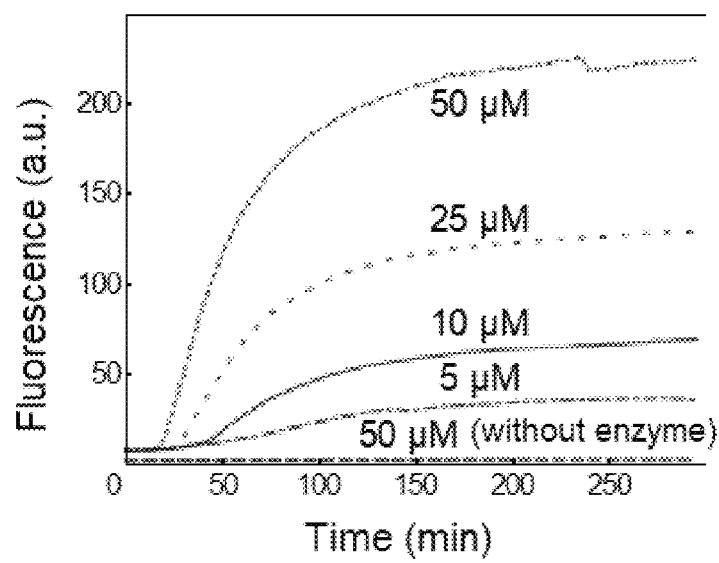
FIG. 3 represents evolutions curves for solid state fluorescence for probe 21 of example 2 at 37° C. (concentrations: 0 μM, 5 μM, 10 μM, 25 μM et 50 μM).

Results:

The results obtained are presented in FIGS. 2 and 3.

Compared to probe 28, probe 13 according to the invention comprising a pair of eliminating/cyclizing spacers makes it possible to reap the benefits of greater response speed while conserving the high stability of the probe in the absence of the target enzyme (false positive signal). Thus, under the same temperature, pH and concentration conditions, probe 13, based on a pair of spacers, has an enzymatic response that is 5 times more rapid than that of probe 28 which comprises only a single spacer. In addition, in the absence of enzyme, probe 13 is stable for more than 15 h and does not generate any measurable fluorescence.

Probes 21 and 27 according to the invention make it possible to benefit from quicker response time while conserving the probe's high stability in the absence of the target enzyme (lack of false positive signal).

Probe 21 was tested at different concentrations: 5 μM, 10 μM, 25 μM and 50 μM. The fluorescence measured is proportional to the concentration of the probe. Fluorescence can be detected at a 5 μM content of the probe.

Example 5

A supernatant of a yeast strain culture, not secreting (A) or secreting (B) a B-glucosidase, was added to probe 21 according to the invention responding to this enzymatic activity. To do this, yeast cells bearing a plasmid that provides hygromycin resistance and bearing, or not, an expression cassette for a secreted beta-glucosidase were cultured for 86 h at 30° C. in 5 mL of a YPD rich medium (10 g of Bacto Peptone Difco, 10 g of Bacto Yeast Extract Difco, 20 g of Glucose, 20 g of Bacto Agar, qsp 1 L distilled water) containing 200 µg/mL of hygromycin. The culture was then centrifuged at 4000 tr/min on an Allegra 25R centrifuge (Beckman/Coulter), in a swash plate TS-5.1-500) at 20° C. and 20 µL of supernatant are taken and added to 180 µL of a PBS1X solution containing the probe substrate at 50 µM. The mixture was then homogenized and incubated 30 minutes at 37° C. The, 10 µL of this mixture were deposited between a microscope slide and cover glass and observed by fluorescence microscope with a 340 nm excitation filter and a 525 nm emission filter.

Figure 4:
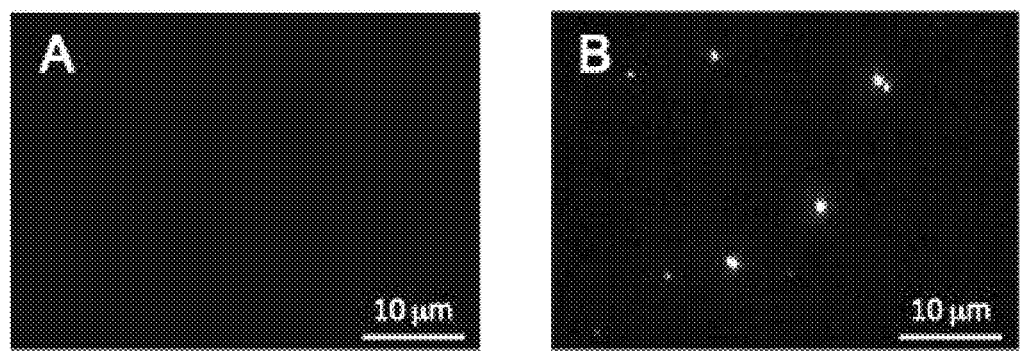
FIG. 4 represents the light signal controlling for the cellulase activity produced by a micro-organism.

The photographs, represented in FIG. 4, were obtained at 100× magnification at immersion on a Zeiss, AX10 microscope.

Fluorescent precipitants (white dots) appear distinctly, which makes it possible to forecast use with high throughput imaging (automated segmentation and quantification).

Example 6

The detection kinetics of cellulase activity in a microorganism culturing medium was evaluated by optical reading on a MITHRAS LB 940 device of the enzymatic activity of a supernatant of a yeast cells culture that secrete ("Supernatant") or which do not secrete ("Control") β-glucosydase.

Yeast culturing is conducted according to the protocol described in example 5 until the obtaining of 20 µL of supernatant. This supernatant is then added to 180 µL of a PBS1X solution containing probe 21 according to the invention at 50 µM in opaque background microplate wells. Signal reading is executed over time on a MITHRAS LB 940 device, after excitation of the probe to 340 nm and collection of the emission at 535 nm.

Figure 5:
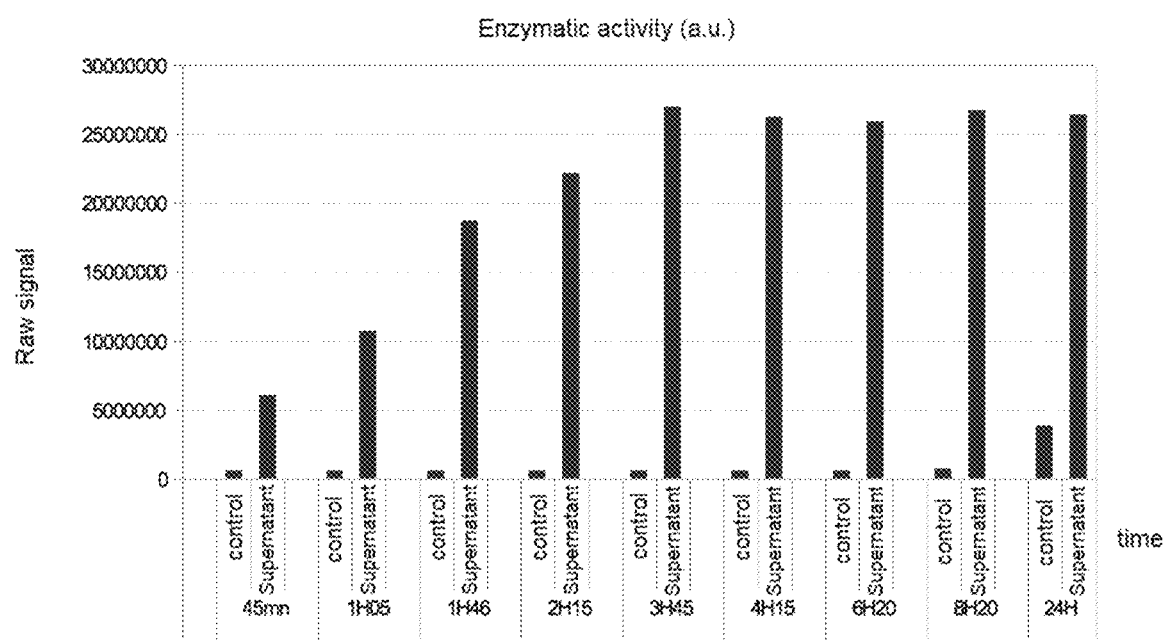
FIG. 5 is a graph representing the detection kinetics of cellulase activity in a micro-organism culturing medium.

The results, shown in FIG. 5, show that the invention makes it possible to detect glycosidase activity secreted into the supernatant after 45 minutes of incubation, that the signal is maximum after 3 h45 m of incubation, and that the signal to noise ratio is about 55 nm.

The invention claimed is:
1. Compounds of formula (I):

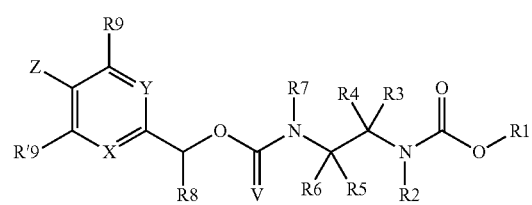

(I)

in which:
R1 is such that HOR1, obtained after cleavage of the —C(O)—OR1 bond present in formula (I), belongs to the class of fluorophores leading to an intramolecular proton transfer in an excited state, called ESIPT,
R3 is an (C1-C4) alkyl or a hydrogen atom and R2 and R4 are bonded together and form, with the carbon and nitrogen atoms to which they are bonded, an aliphatic heterocycle which can be substituted by a water-solubilizing group,
R5 and R6 are identical or different and represent, independently of each other, a hydrogen atom, an (C1-C4) alkyl, or an (C5-C10)aryl,
R7 is selected from the group consisting of hydrogen atom, a (C1-C4) alkyl and (C1-C4) alkoxy,
R8 represents a hydrogen atom or a (C1-C10) alkyl group, non-substituted or substituted by one or more substituents selected from the group consisting of chlorine, bromine, iodine, fluorine, cyano, alkyl, trifluoralkyl, trifluoromethyl, alkenyl, alkynyl, cycloalkyl, aryl, hetero-aryl, heterocyclo-alkyl, amino, alkylamino, diaklyamino, hydroxy, alkoxy, aryloxy, alkoxycarbonyl and aryloxycarbonyl,
or R8 represents a -D1-D2-D3 group with:
D1 representing a triazolyl or —CH2-triazolyl group,
D2 representing an (C1-C10) alkylene, (C1-C10) alkenylene or (C1-C10) alkynylene group, said groups possibly being interrupted by one or more selected from the group consisting of O, N, a divalent glycosyl group, an —O—(CHR—CHR')n-, —N—(CHR—CHR'—O)n- group, n being an integer varying from 1 to 20, R and R', identical or different, representing H or CH3 upon condition that R and R' are not simultaneously CH3, an amino acid or a peptide, and a combination of these groups,
D3 representing a maleimidocaproyl motif, amino acid, peptide, folic acid, antibody or antibody fragment bonded to D2, by a carboxylic acid function comprised in it, forming an ester or amide bond,
R9 and R'9, identical or different, represent a hydrogen atom, an electron-withdrawing group, or a —NH—C(O)—CH2-Ab group, with Ab representing an antibody,
V represents an oxygen atom or a sulfur atom,
X, Y and Z are such that:
either X represents CR10, Y represents CR'10 and Z represents OR0,
or X represents CR10, Y represents COR0 and Z represents R'10,
or X represents CR10, Y represents a nitrogen atom and Z represents OR0,
or X represents a nitrogen atom, Y represents COR0 and Z represents R10 with:
R0 representing a glycosyl group bound by its anomeric carbon atom to the rest of the molecule of formula (I), and
R10 and R'10, identical or different, representing a hydrogen atom or an electron-donating group,
in the form of a mixture of optical isomers according to all proportions, or in an optical isomer enriched form.
2. Compounds (I) according to claim 1, wherein R3 is a hydrogen atom or an (C1-C4) alkyl, and R2 and R4 are bonded to each other and form a —(CH2)m- chain with m=3, 4 or 5.
3. Compounds (I) according to claim 1, wherein R3 is a hydrogen atom or an (C1-C4) alkyl, and R2 and R4 are bonded to each other and form a —CH2CH2-NR11-CH2- chain in the direction of R2 toward R4, R11 representing a hydrogen atom or -(L)n-GP with n which is equal to 0 or 1, L a linking arm and GP a water-solubilizing group.
4. Compounds (I) according to claim 1, wherein R1 is an aromatic group comprising one or more aromatic rings, which rings can comprise one or more hetero-atoms selected from the group consisting of nitrogen, oxygen, sulfur, and/or one or more carbon atoms in the form of a C=O carbonyl, and said aromatic rings being not substituted or substituted by one or more substituents selected from the group consisting of chlorine, bromine, iodine, fluorine, cyano, alkyl, trifluoroalkyl, trifluoromethyl, alkenyl, alkynyl, cycloalkyl, aryl, hetero-aryl, heterocyclo-alkyl, amino, alkylamino, diaklyamino, hydroxy, alkoxy, aryloxy, alkoxycarbonyl and aryloxycarbonyl.

5. Compounds (I) according to claim 1, wherein R1 is an aromatic group with —OR1 according to formula (A1):

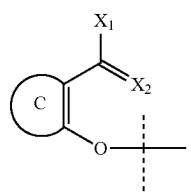

(A1)

in which:
either X2 is an oxygen atom and X1 is a —NH2, —OH, —SH, (C1-C20) alkyl, (C5-C24) aryl, —O—(C1-C20) alkyl, —O-phenyl, —NH—(C1-C20) alkyl or —NH-phenyl, —S—(C1-C20) alkyl or —S—(C5-C24) aryl group, said alkyl and phenyl groups being non-substituted or substituted by one or more substituents selected from the group consisting of chlorine, bromine, iodine, fluorine, cyano, alkyl, trifluoroalkyl, trifluoromethyl, alkenyl, alkynyl, cycloalkyl, aryl, hetero-aryl, heterocyclo-alkyl, amino, alkylamino, diaklyamino, hydroxy, alkoxy, aryloxy, alkoxycarbonyl and aryloxycarbonyl, Or X2 represents a nitrogen atom and is bound to X1 which then represents CH, O, S, N or, NH to form a (C5-C24) hetero-aryl, not substituted or substituted by one or more substituents selected from the group consisting of chlorine, bromine, iodine, fluorine, cyano, alkyl, trifluoroalkyl, trifluoromethyl, alkenyl, alkynyl, cycloalkyl, aryl, hetero-aryl, heterocyclo-alkyl, amino, alkylamino, diaklyamino, hydroxy, alkoxy, aryloxy, alkoxycarbonyl and aryloxycarbonyl,

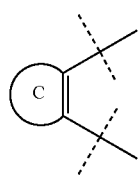

represents an (C5-C24) aryl or a (C5-C24) hetero-aryl, non-substituted or substituted by one or more substituents selected from the group consisting of chlorine, bromine, iodine, and fluorine, cyano, alkyl, trifluoroalkyl, trifluoromethyl, alkenyl, alkynyl, cycloalkyl, aryl, hetero-aryl, heterocyclo-alkyl, amino, alkylamino, diaklyamino, hydroxy, alkoxy, aryloxy, alkoxycarbonyl and aryloxycarbonyl.

6. Compounds (I) according to claim 1, wherein R1 is an aromatic group with —OR1 according to one of the following formulas (A4) or (A5):

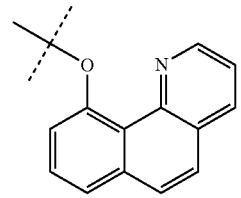

(A4)

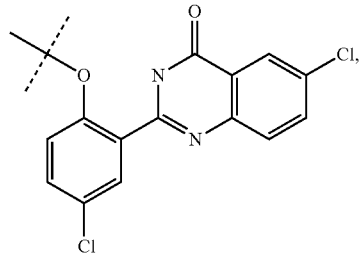

(A5)

7. Compounds (I) according to claim 1, wherein R0 is cleavable from the rest of compound (I) by the catalytic action of a glycosidase.

8. Compounds (I) according to claim 1, wherein R0 is a group that is cleavable under the action of a glycosidase, selected from the group consisting of N-acetyl-β-galactosaminidase; N-acetyl-β-glucosaminidase; α-amylase; α-arabinofuranosidase, α-arabinosidase; β-cellobiosidase; β-chitobiosidase; α-galactosidase; β-galactosidase; α-glucosidase; β-glucosidase; β-glucuronidase; α-maltosidase; α-mannosidase; β-mannosidase; β-xylosidase; β-D-fucosidase; α-L-fucosidase, β-L-fucosidase; L-iduronidase and cellulase; and R0 is a mono-glycosylated group bound by its anomeric carbon atom, selected from the group consisting of galactosyl, glucosyl, mannosyl, gulosyl, allosyl, altrosyl, idosyl, talosyl, fucosyl, fructosyl, arabinosyl, lyxosyl, ribosyl, xylosyl, glucuronyl and N-acetyl-hexosaminyl, and a polyglycosylated group constituted of several of these monoglycosylated groups, identical or different.

9. Compounds (I) according to claim 1, wherein R5 and R6 are identical and represent a hydrogen atom.

10. Compounds according to claim 1, wherein R7 represents a hydrogen atom or an (C1-C4) alkyl group.

11. Compounds (I) according to claim 1, wherein R8 represents a hydrogen atom.

12. Compounds (I) according to claim 1, wherein V represents an oxygen atom.

13. Compounds (I) according to claim 1, wherein X, Y and Z are such that:
either X represents CR10, Y represents CR'10 and Z represents OR0,
or X represents CR10, Y represents COR0 and Z represents R'10, with R10, R'10 and R0 as defined in claim 1.

14. Compounds (I) according to claim 1, wherein at least one of groups R9 or R'9 represents a halogen atom, a —NO2 group, or a —CN group.

15. Compounds (I) according to claim 1, wherein R10 and, if present, R'10 are identical and represent a hydrogen atom.

16. Compounds (I) according to claim 1 of formula (Ia):

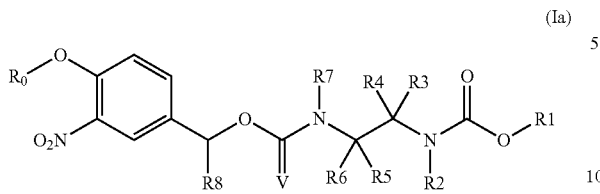
(Ia)

where R1, R2, R3, R4, R5, R6, R7, R8, R0 and V are as defined in claim 1, in the form of a mixture of optical isomers according to all proportions, or in an enriched form in an optical isomer.

17. Compounds (I) according to claim 1 of formula (Ib):

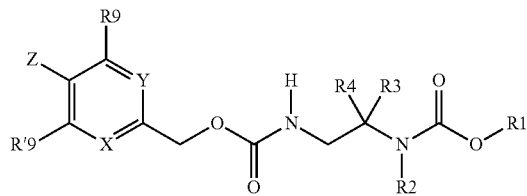
(Ib)

where R1, R2, R3, R4, R9, R'9, X, Y and Z are as defined in claim 1, in the form of a mixture of optical isomers according to all proportions, or in an enriched form in an optical isomer.

18. Compounds (I) according to claim 1 of formula (Ic):

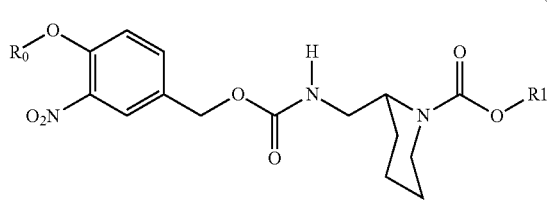
(Ic)

where R0 and R1 are as defined in claim 1, in the form of a mixture of optical isomers according to all proportions, or in an enriched form in an optical isomer.

19. Process for the preparation of a compound of formula (I) according to claim 1 comprising the following steps:

providing a compound (II) of formula

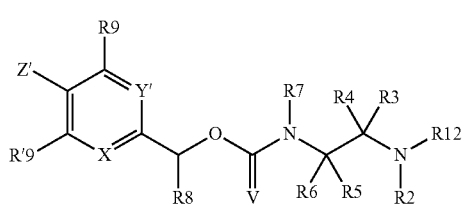
(II)

providing a compound (III) of formula

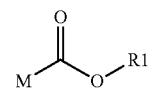
(III)

obtaining compound (IV) by addition reaction of said compound (II) to compound (III), said compound (IV) having the formula:

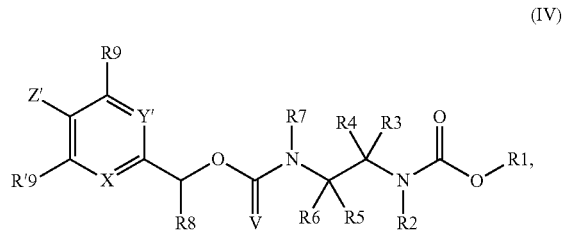
(IV)

and
deprotecting the alcohol functions present in the R'0 group of said compound (W) in order to obtain said compound (I),
wherein in the formulas:
R1, R2, R3, R4, R5, R6, R7, R8, R9, R'9 and V are as defined in claim 1,
R12 represents a hydrogen atom, or an amine functions protecting group,
X, Y' and Z' are such that:
either X represents CR10, Y' represents CR'10 and Z' represents OR'0,
or X represents CR10, Y' represents COR'0 and Z' represents R'10,
or X represents CR10, Y' represents a nitrogen atom and Z' represents OR'0,
or X represents a nitrogen atom, Y' represents COR'0 and Z' represents R10,
with R'0 representing a R0 group of which all of the alcohol functions are protected by a protecting group, and R0, R10 et R'10 are as defined in claim 1,
M represents a leaving group.

20. Compounds (I) according to claim 5, wherein

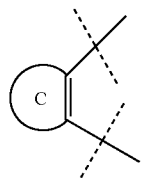

represents a (C5-C24) aryl or a (C5-C24) hetero-aryl selected from the group consisting of phenyl, naphthyl, and:

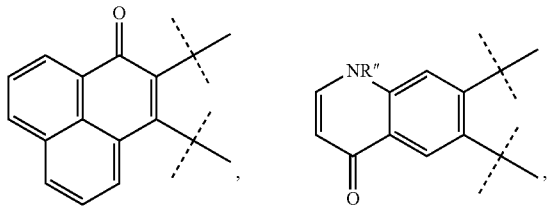

-continued

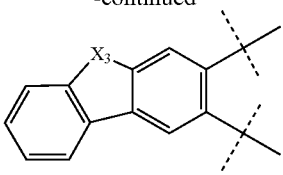

said groups being non-substituted or substituted by one or more substituents selected from the group consisting of chlorine, bromine, iodine, fluorine, cyano, alkyl, trifluoroalkyl, trifluoromethyl, alkenyl, alkynyl, cycloalkyl, aryl, hetero-aryl, heterocyclo-alkyl, amino, alkylamino, diaklyamino, hydroxy, alkoxy, aryloxy, alcoxycarbonyl and aryloxycarbonyl, with X3 which represents S, O or NRd and Rd which represents a hydrogen atom or a (C1-C4) alkyl group.

21. Compounds (I) according to claim 5, wherein OR1 is of the phenoxy type and corresponds to one of the following structures (A2) or (A3):

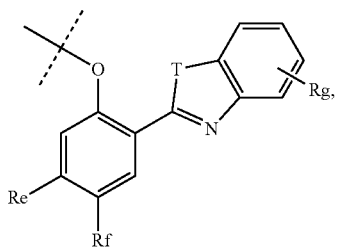
(A2)

in which:
T is —NH—C(O)—, —S—, —O—, —NH—, —N((C1-C20) alkyl)- or —N(C5-C24)aryl)-, Re is a hydrogen atom or an electron-withdrawing carbonaceous substituent, or Re is —CONRiRj, with Ri and Rj, identical or different, which represent a hydrogen atom, or an (C1-C4) alkyl group, or Re is —CF3, or a 2-oxazolyl, 2-thiazolyl, 2-imidazolyl, 2-benzo imidazolyl, 4-pyrimidinone-2-yl or quinazolinone-2-yl group, Rf is a hydrogen atom, a chlorine, bromine, iodine or fluorine atom, —OH, —NH2, —NRkRl, —NHRk or —ORk, with Rk and Rl, identical or different, which each, independently, represent an (C1-C4) alkyl group, Or Re and Rf are bonded to each other to form a hydrocarbon chain comprising 4 or 5 members, saturated or unsaturated, substituted or non-substituted, possibly interrupted by one or more hetero-atoms selected from the group consisting of N, S and O, Rg is a hydrogen, Br, Cl, I or F atom,

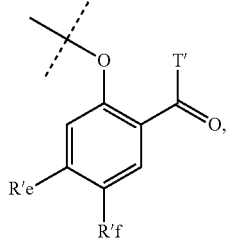
(A3)

in which:
T' is —NH2, —OH, an (C5-C24) aryl group, an (C1-C4) alkyl group, —SH, —NHR'g, —OR'g, —NR'gRh' or —SR'g, R'g and Rh', identical or different, representing an (C1-C4) alkyl or aryl group, R'e is a hydrogen atom or an electron-withdrawing carbonaceous substituent, or R'e is —CONR'jR'k, with R'j and R'k, identical or different, which represent a hydrogen atom, or an (C1-C4) alkyl group, or R'e is —CF3, or a 2-oxazolyl, 2-thiazolyl, 2-imidazolyl, 2-benzo imidazolyl, 4-pyrimidinone-2-yl or quinazolinone-2-yl group, R'f is a hydrogen, chlorine, bromine, iodine or fluoride atom, —OH, —NH2, —NR'lR'm or —OR'l, with R'l and R'm, identical or different, which represent an (C1-C4) alkyl group, or Re and Rf' are bonded to each other to form a hydrocarbon chain comprising 4 or 5 members, saturated or unsaturated, substituted or non-substituted, possibly interrupted by one or more hetero-atoms selected from the group consisting of N, S and O.

* * * * *